United States Patent
Chang et al.

(10) Patent No.: US 9,156,874 B2
(45) Date of Patent: Oct. 13, 2015

(54) DOUBLE-LIVER-TARGETING PHOSPHORAMIDATE AND PHOSPHONOAMIDATE PRODRUGS

(71) Applicant: Nanjing Molecular Research, Inc., Nanjing (CN)

(72) Inventors: Junbiao Chang, Zhengzhou (CN); Qiang Huang, Suzhou (CN); Runcong Liu, Philadelphia, PA (US); Zheng Wang, Suzhou (CN)

(73) Assignee: Nanjing Molecular Research, Inc. (CN)

( * ) Notice: Subject to any disclaimer, the term of this patent is extended or adjusted under 35 U.S.C. 154(b) by 180 days.

(21) Appl. No.: 13/838,071

(22) Filed: Mar. 15, 2013

(65) Prior Publication Data
US 2013/0210757 A1    Aug. 15, 2013

Related U.S. Application Data

(63) Continuation-in-part of application No. PCT/US2011/068131, filed on Dec. 30, 2011.

(60) Provisional application No. 61/460,458, filed on Jan. 3, 2011, provisional application No. 61/689,936, filed on Jun. 16, 2012.

(51) Int. Cl.
| | | |
|---|---|---|
| A61K 31/70 | (2006.01) | |
| A01N 43/04 | (2006.01) | |
| C07H 19/10 | (2006.01) | |
| C07H 19/12 | (2006.01) | |
| C07H 19/20 | (2006.01) | |
| C07F 9/6561 | (2006.01) | |
| C07F 9/6558 | (2006.01) | |
| C07H 19/06 | (2006.01) | |
| C07H 19/073 | (2006.01) | |
| C07H 19/09 | (2006.01) | |
| C07H 19/16 | (2006.01) | |
| C07H 19/173 | (2006.01) | |
| C07H 19/19 | (2006.01) | |
| C07H 19/207 | (2006.01) | |
| C07D 405/04 | (2006.01) | |
| C07D 473/34 | (2006.01) | |
| C07D 473/40 | (2006.01) | |
| C07F 9/26 | (2006.01) | |
| C07F 9/24 | (2006.01) | |

(52) U.S. Cl.
CPC .............. *C07H 19/10* (2013.01); *C07D 405/04* (2013.01); *C07D 473/34* (2013.01); *C07D 473/40* (2013.01); *C07F 9/65586* (2013.01); *C07F 9/65616* (2013.01); *C07H 19/06* (2013.01); *C07H 19/073* (2013.01); *C07H 19/09* (2013.01); *C07H 19/12* (2013.01); *C07H 19/16* (2013.01); *C07H 19/173* (2013.01); *C07H 19/19* (2013.01); *C07H 19/20* (2013.01); *C07H 19/207* (2013.01); *C07F 9/2429* (2013.01); *C07F 9/26* (2013.01)

(58) Field of Classification Search
None
See application file for complete search history.

(56) References Cited

U.S. PATENT DOCUMENTS

| | | |
|---|---|---|
| 2006/0142238 A1 | 6/2006 | McGuigan |
| 2009/0169504 A1 | 7/2009 | Sommadossi et al. |
| 2009/0306007 A1 | 12/2009 | Wagner |

OTHER PUBLICATIONS

Gardelli et al. J. Med. Chem. (2009), vol. 52, pp. 5394-5407.*

* cited by examiner

*Primary Examiner* — Patrick Lewis
(74) *Attorney, Agent, or Firm* — Fox Rothschild LLP; Wansheng Jerry Liu

(57) ABSTRACT

This application discloses phosphoramidate and phosphonoamidate prodrugs of alcohol-based therapeutic agents, such as nucleosides, nucleotides, acyclonucleosides, C-nucleosides, and C-nucleotides, and use of these prodrugs for treatment of diseases or disorders, including infectious diseases and cancers. This application also discloses a general method for enhancing bioavailability and/or liver-targeting property of alcohol drugs through converting the alcohol drugs to phosphoramidate or phosphonoamidate prodrugs, and methods of preparation of these prodrugs.

20 Claims, 4 Drawing Sheets

DOUBLE-LIVER-TARGETING PHOSPHORAMIDATE AND PHOSPHONOAMIDATE PRODRUGS

CROSS REFERENCE TO RELATED APPLICATIONS

This application claims priority under 35 U.S.C. §119(e) to U.S. Provisional Application Ser. No. 61/689,936, filed Jun. 16, 2012, and is also a continuation-in-part application of International Application Ser. No. PCT/US2011/068131, filed Dec. 30, 2011, which in turn claims priority under 35 U.S.C. §119(e) to U.S. Provisional Patent Application Ser. No. 61/460,458, filed Jan. 3, 2011, all of which are incorporated by reference in their entirety.

FIELD OF THE INVENTION

The present invention relates to double-liver-targeting phosphoramidate or phosphonoamidate prodrugs, and therapeutic use and preparation methods thereof.

BACKGROUND OF THE INVENTION

Nucleoside analogues have been developed as antiviral and anticancer agents. Nucleotide kinases phosphorylate nucleosides to their corresponding 5'-monophosphates which are further converted into their di- and tri-phosphates by cellular nucleotide kinases.

Some nucleosides are weakly active because they cannot be efficiently phosphorylated by kinases or are not substrates of kinases at all, as evidenced by the observation that some inactive nucleosides, when converted chemically to triphosphates, become potently active against certain viruses in vitro. Nucleoside phosphates (nucleotides) per se cannot be used as drugs often because they are de-phosphorylated by membrane nucleotides and/or other hydrolases before entering the cells or are too polar to enter the cells. To improve biological activity of nucleosides, their phosphate prodrugs have been intensively studied because they can potentially bypass the rate-limiting first step of phosphorylation. Recently, phosphoramidate prodrug approach has been reported to be an effective method to convert biologically inactive nucleosides to their active nucleoside monophosphates bypassing the rate-limiting first step of phosphorylation (see, e.g., J. Med. Chem. 2007, 50, 5463; WO 2008/121634; WO 2008/082601; and WO 2008/082602). In recent years, there are a number of patent applications reporting utilization of the phosphoramidates as prodrugs to deliver nucleoside monophosphates to tissues, such as liver (see U.S. Pat. No. 6,455,513; WO 2009/052050; WO 2008/121634; WO 2008/0833101; WO 2008/062206; WO 2007/002931; WO 2008/085508; WO 2007/095269; WO 2006/012078; and WO 2006/100439). The nucleoside monophosphates can be further phosphorylated to diphosphates and then the corresponding biologically active triphosphates.

However, the above-mentioned phosphoramidate approaches based on McGuigan's technology (U.S. Pat. No. 6,455,513) have various limitations due to potential neurotoxicity and liver and kidney damages caused by phenol released from prodrugs (Carcinogenesis 1993, 14, 2477; Mutat. Res. 1991, 249, 201).

McGuigan's phosphoramidate of nucleoside usually can demonstrate maximum biological activity in cell line assays because it can release nucleoside or nucleotide quickly in the cells. It was reported that phosphoramidate prodrug of d4T could not be detected in plasma after oral administration immediately (Drug Metab. Dispos. 2001, 29, 1035). Phosphoramidate is stable in gastric fluid and may be absorbed in the stomach. On the other hand, phosphoramidate may decompose readily in intestinal fluid to ala-d4T-MP which may not be absorbed efficiently in intestine due to its polar nature. Therefore, bioavailability of this type of phosphoramidate prodrugs usually is low, probably due to its hydrolysis catalyzed by esterase followed by releasing phenol. For example, the bioavailability of GS-7340, an isopropylalanyl monoamidate phenyl monoester of tenofovir, was only 17% in male beagle dogs (Antimicrob. Agents Chemother. 2005, 49, 1898). Phosphoramidate prodrug of 2'-C-methylguanosine only delivered about 10%-20% of active triphosphate delivered into the liver from free nucleoside (J. Med. Chem. 2010, 53, 4949).

Efforts to search for phosphate prodrugs that would be cleaved by an esterase independent mechanism have led to the discovery of HepDirect prodrugs (J. Med. Chem. 1994, 37, 498; J. Am. Chem. Soc. 2004, 126, 5154; J. Pharmacol. Exp. Ther. 2005, 312, 554). Erion et al. disclosed that cyclic phosphate or phosphonate prodrugs which are stable in the presence of esterase can enhance liver specific drug delivery (Erion, M., et al., U.S. Pat. No. 7,303,739 and reference thereof). Erion's prodrugs are activated by P450 enriched in the liver. However, clinical application of this approach may be limited by potentially adverse side effects caused by α,β-unsaturated ketone metabolites from prodrugs.

In the McGuigan's prodrugs, as shown in the general phosphoramidate structure of formula F1, $R^a$ is aminoacid ester residue while $R^b$ is an aryl group including phenyl or nathphyl. $R^b$ would be simultaneously released after ester of aminoacid residue was hydrolyzed by esterase. Sofia (U.S. Pat. No. 7,964,580) reported only one phosphoramidate with $R^a$ as L-alanyl isopropyl ester and $R^b$ as phenyl group. Although $R^b$ was defined as an alkyl group, such as Me, Et, iPr, and t-Bu, there is no phosphoramidate prodrug with $R^b$ as alkyl group that has actually been prepared. WO 2012/142075 also reported phosphoramidates with $R^b$ as benzyl groups with no substitution on phenyl group. However, no biological activity for any of such compounds was reported. Therefore, phosphoramidates with $R^b$ as alkyl or benzyl group without substitution on phenyl ring have never demonstrated biological usefulness, probably because these groups (alkyl or benzyl group) in phosphoramidate prodrugs of nucleoside are too stable to be cleaved efficiently to produce active nucleoside phosphate.

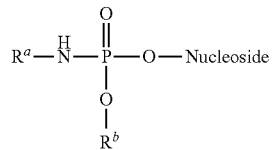

F1

Therefore, new prodrug forms of nucleoside or nucleotide compound are still being actively pursued.

SUMMARY OF THE INVENTION

The present inventors surprisingly discovered that substitution, such as methyl substitution, on the phenyl ring of the benzyl group of a phosphoramidate prodrug significantly improved the process of activation of the prodrugs (see WO 2012/094248). The unsubstituted benzyl phosphoramidate (F2) did not show any anti-HCV activity while the 2-methylbenzyl benzyl phosphoramidate (F3) demonstrated potent anti-HCV activity in an replicon assay.

The fact that the 2-methylbenzyl benzyl phosphoramidate prodrug (F3) demonstrated potent anti-HCV activity indicated that the prodrug F3 can be activated to release active nucleoside phosphate efficiently in vitro. However, bioavailability of 2-methylbenzyl benzyl phosphoramidate (F4) of Floxuridine was very low in rats. To discover orally available phosphate prodrug, we prepared an analog of phosphoramidate F4, having a structure of formula F5, in which the benzylamine was replaced with an aminoacid ester moiety. It was discovered that the phosphoramidate prodrug of F5, which contains an aminoacid ester moiety and the 2-methylbenzyl group had significantly improved oral bioavailability as compared with the phosphoramidate of formula F4. The phosphoramidate prodrug of formula F5 is the first example that has demonstrated excellent ability to deliver nucleoside phosphoramidate into the liver in rats after oral administration (see Example 17). Therefore, this novel phosphoramidate prodrug containing the aminoacid ester and substituted benzyl groups can be used as liver-targeting prodrug to deliver active nucleoside phosphoramidate into the liver for treating liver diseases, by which the systemic toxicity can be significantly reduced due to the reduced concentration of the active drug in the circulation system. Without intending to be bound by theory, the working mechanisms of the prodrug disclosed herein may include hydrolysis of the ester group by an esterase enriched in the liver while the substituted benzyl group is degraded through hydroxylation by P450, which is also highly enriched in the liver. Therefore, the phosphoramidate prodrugs of the present invention can be considered as double-liver-targeting prodrugs. Compound F5 was synthesized as a single isomer. The chirality of F5 was tentatively assigned based on the similar chemistry and will be confirmed by X-ray crystallography.

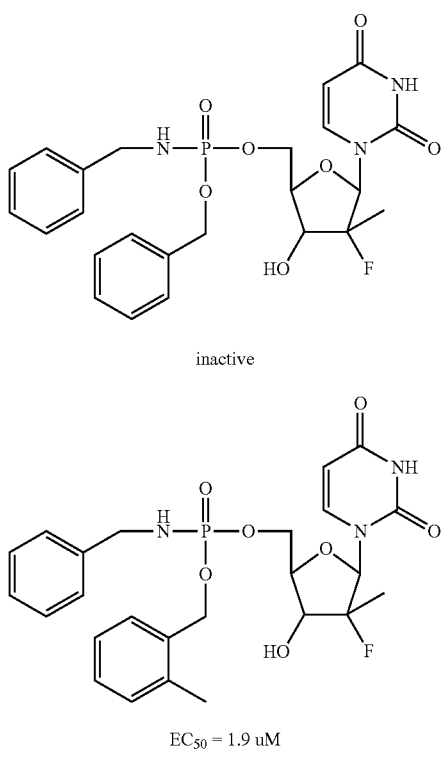

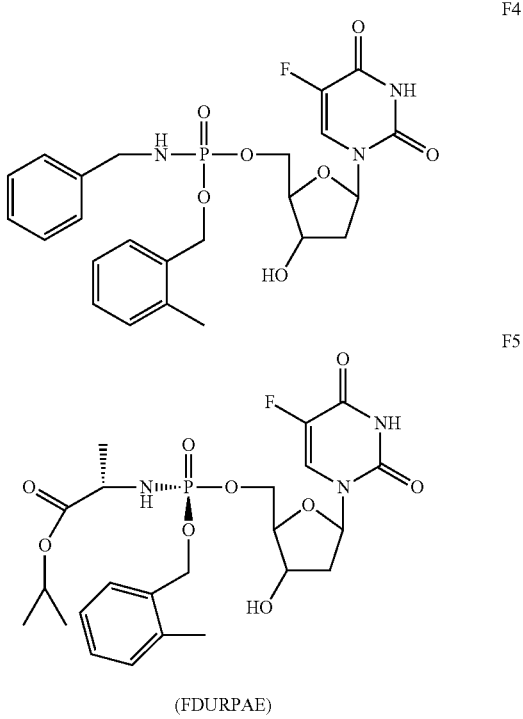

(FDURPAE)

A stable DGX-intermediate prodrug of formula F7 was prepared and isolated as a carboxylic acid or its salt (only salt form shown in FIG. 1). Even if the DGX-prodrug of formula F5 is hydrolyzed by esterases in organs other than the liver, the stable intermediate prodrug (F7) formed could still be delivered into the liver by rich monocarboxylate transporters. While McGuigan's prodrug (F6) would be converted to a polar diacid (F9) after hydrolysis of the ester group by esterases followed by simultaneous release of phenol, the stable DGX-intermediate prodrug of formula F7 can be prepared as a water-soluble phosphoramidate prodrug.

One of the objectives of the present invention is to provide double-liver-targeting nucleoside monophosphate prodrugs with aminoacid ester and substituted benzyl group. Another objective of the present invention is to provide water-soluble and liver-targeting nucleoside phosphoramidate or phosphonoamidate prodrugs containing an aminoacid salt moiety and a substituted benzyl group. Another objective of the present invention is to provide orally available phosphoramidate or phosphonoamidate prodrugs for nucleoside drugs that cannot be administered orally due to their instability in the gastrointestine track. Another objective of the present invention is to provide compositions comprising one or more of the compounds disclosed herein for therapeutic uses similar to the uses of their parent drugs. Another objective of the present invention is to provide compounds and compositions of the present invention for treating diseases which may be resistant to their parent drugs. Another objective of the present invention is to provide therapeutic uses of compounds and compositions thereof disclosed herein in combination with other therapeutically useful agents. Another objective of the present invention is to provide the synthetic methods and processes for preparing the compounds of the nucleoside phosphoramidate or phosphonoamidate prodrugs disclosed herein as single isomers.

The present invention provides prodrug forms of small molecule drug substances, in particular, nucleosides, nucleotides, C-nucleosides, C-nucleotides, nucleoside phosphonates. Without intending to bound by theory, the prodrugs with aminoacid ester and substituted benzyl groups disclosed herein are activated by both esterases and P450 enriched in the liver, and deliver the active drugs, or nucleoside phosphoramidate or phosphonoamidates, into the liver efficiently, which have demonstrated double-liver-targeting nature and usefulness particularly as prodrugs for treating liver diseases, including but not limited to liver cancers and hepatitis infections. The present invention also provides prodrug forms administered orally for small molecules that cannot be taken orally due to their metabolic instability in gastrointestinal track.

In one embodiment, the present invention provides a compound of formula I:

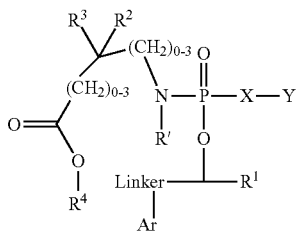

or a pharmaceutically acceptable prodrug, salt, solvate, or stereoisomer thereof, wherein:

X is oxygen (O) or —CH$_2$—;

Y is a nucleoside, acyclonucleoside, or C-nucleoside moiety; R', R$^1$, R$^2$, and R$^3$ are independently selected from the group consisting of hydrogen and substituted and unsubstituted alkyl, aryl, alkynyl, alkenyl, cycloalkyl, heterocyclyl, and heteroaryl groups, wherein the heterocyclyl and heteroaryl group each comprises one to three heteroatoms independently selected from O, S, and N, or alternatively R$^2$ and R$^3$ together with the carbon atom to which they are attached form an optionally substituted 3- to 8-, preferably 3- to 6-, membered ring;

R$^4$ is selected from the group consisting of hydrogen, and substituted or unsubstituted alkyl, aryl, alkynyl, alkenyl, cycloalkyl, heterocyclyl, and heteroaryl groups, metal ions, and ammonium ions; and Ar is optionally substituted aryl or heteroaryl, wherein the heteroaryl comprises one to three heteroatoms independently selected from O, S, and N, wherein said optionally substituted aryl is preferably C$_6$-C$_{10}$ aryl, in particular phenyl or naphthyl, and said optionally substituted heteroaryl is preferably a 5- to 10-membered heteroaryl; and the "linker" is selected from a bond and optionally substituted C$_1$-C$_3$ alkylene, vinyl, ethynyl, arylene and heteroarylene groups, optionally substituted vinyl, or ethynyl or aromatic or heteroaromatic moiety, wherein the heteroarylene comprises one to three heteroatoms independently selected from O, S, and N.

As would be appreciated by those skilled in the art, the formulas of Y—XH or Y—OH according to the present invention would represent a nucleoside, acyclonucleoside, or C-nucleoside drug; the formula Y—O—P(O)(OH)$_2$ would represent a biologically active monophosphate of a nucleoside, acyclonucleoside, or C-nucleoside drug; and the formula Y—CH$_2$—P(O)(OH)$_2$ would represent a biologically active phosphonate analog of a nucleoside, acyclonucleoside, or C-nucleoside drug.

In another unique aspect, prodrugs disclosed herein can also be prepared and used as water soluble salts, which possess unique useful properties as compared with any other phosphoramidate prodrugs reported in the literature. Salt forms of phosphoramidate prodrugs herein can be salts formed with organic or inorganic bases. For example, when R$^4$ is an ammonium ion, it can be NH$_4^+$ or an organic ammonium ion, including but not limited to monoalkyl, dialkyl, trialkyl, and tetraalkyl ammonium ions, for example, RNH$_3^+$, R$_2$NH$_2^+$, R$_3$NH$^+$, or R$_4$N$^+$, wherein R represents a lower alkyl group, preferably comprising one to six carbons, more preferably comprising one to four carbons. When R$^4$ is a metal ion, it can be any pharmaceutically acceptable metal ion, preferably K$^+$, Na$^+$, Ca$^{2+}$, Mg$^{2+}$, or the like. However, carboxylic acid intermediates of typical McGuigan's phosphoramidate prodrugs are unstable and readily decompose to very polar diacids after simultaneously releasing phenol under ester hydrolysis or physiological conditions.

In another aspect, the present invention provides a method for efficient delivery of nucleoside phosphates or phosphonates into cells, particularly into the liver, through use of the phosphoramidate and phosphonoamidate prodrugs disclosed herein.

In another aspect, the present invention provides use of a compound as described herein as a prodrug of nucleoside, acyclic nucleoside, C-nucleoside, nucleotide, or a phosphonate analog thereof. In some embodiments, the compounds of the present invention can be used in combination with other therapeutically active agents.

In another aspect, the present invention provides a pharmaceutical composition comprising any compound disclosed herein, and a pharmaceutically acceptable carrier or diluent.

In another aspect, the present invention provides a method of treating diseases, such as a viral infection or cancer, comprising administration of any compound as disclosed herein, or a pharmaceutically acceptable prodrug thereof, to a patient in need of the treatment.

In another aspect, the present invention provides a method of treating diseases, such as a viral infection or cancer, comprising administration of a pharmaceutical composition as disclosed herein to a patient in need of the treatment.

In another aspect, the present invention provides use of any compound disclosed herein in the manufacture of a medicament for treatment of diseases, such as viral infections or cancers.

In another aspect, the present invention provides processes and intermediates for the preparation of the phosphoramidate prodrugs disclosed herein as a diastereomerically enriched isomer.

These and other aspects of the present invention will be better appreciated by reference to the following detailed description and claims.

DETAILED DESCRIPTION OF THE INVENTION

Figure 1:
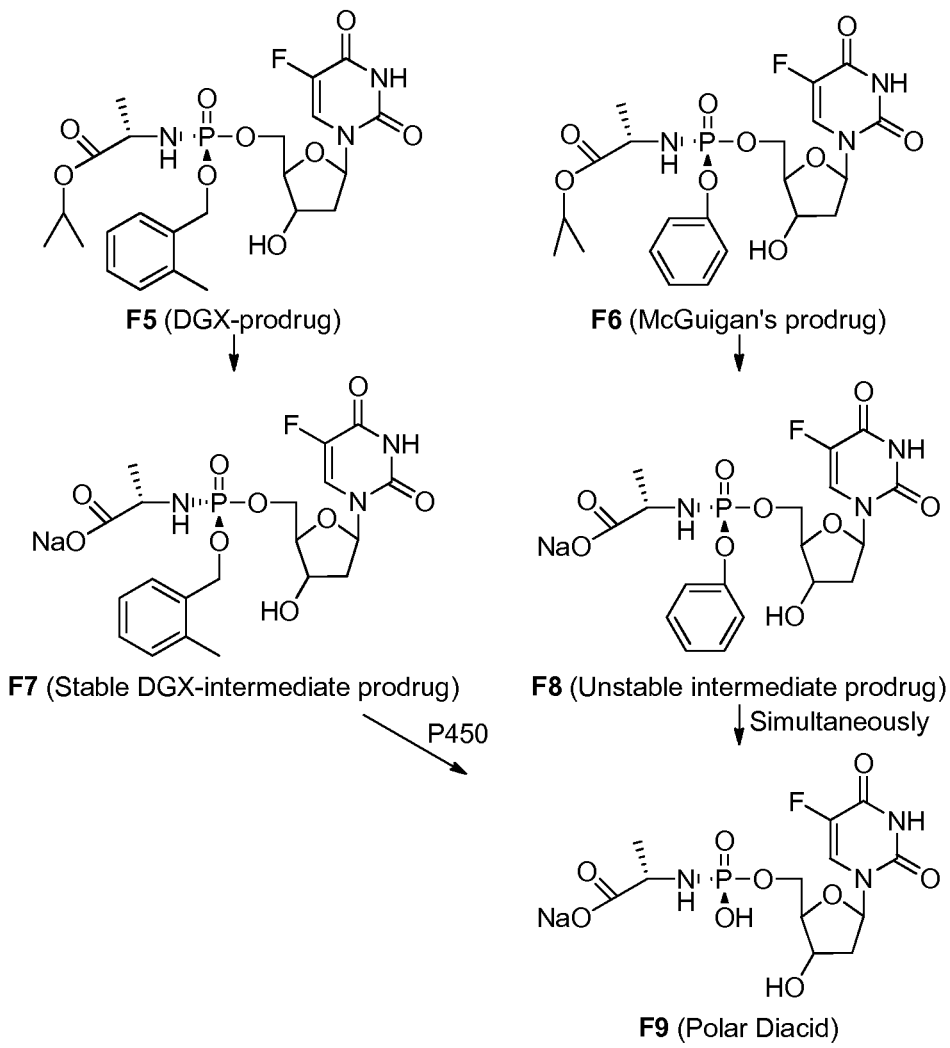
FIG. 1 illustrates prodrug activation pathways.

The present invention relates to chemical compounds that have enhanced therapeutic potency, particularly potency with respect to cancers (such as leukaemia), viral infections (including HIV, HBV and HCV), liver disorders (including liver cancer), and metabolic diseases (such as diabetes, hyperlipidemia, atherosclerosis, and obesity).

In one aspect, the present invention provides phosphoramidate or phosphonoamidate prodrugs of a variety of therapeutic agents, including nucleosides, nucleotides, C-nucleosides, C-nucleotides, and other alcohol-containing drugs, or phosphonate analogs thereof.

In one preferred embodiment of the present invention, the phosphoramidate and phosphonoramidate prodrug comprises optionally substituted benzyl group and aminoacid moiety, the benzyl group preferably substituted by one or more substituents independently selected from $C_1$-$C_4$ alkyl, $C_1$-$C_4$ alkoxy, $C_1$-$C_4$ haloalkoxy, hydroxy, halogen, substituted amino, acylamino.

In certain embodiments, while not being limited to any theory, the parent drug compound is mainly obtained from selective metabolism of a phosphoramidate or phosphonoamidate compound in the liver; thus, the parent drug is capable of accumulating in the liver, for example, of humans. By selectively targeting and activating compounds in the liver, the potentially undesired distribution of the active compound in the gastrointestinal track or plasma can be reduced.

In certain embodiments, the prodrugs of the present invention, derivatized from inactive nucleosides, may become biologically active, since the prodrugs directly deliver nucleoside monophosphate bypassing the rate-limiting first step of phosphorylation.

Since these methods disclosed herein allow accumulation of the nucleoside phosphate or phosphonate compounds in the liver (in particular, of humans), the methods described herein can be useful, for example, for treatment and/or prophylaxis of diseases or disorders of the liver, such as liver cancers and hepatitis B or C.

A method for the treatment of a liver disorder is also provided, which includes administering an effective amount of a compound provided herein, either alone or in combination or alternation with another therapeutically effective agent, optionally in a pharmaceutically acceptable carrier.

Prodrugs with high lipophilicity of the present invention readily penetrate cell membranes so as to improve pharmacokinetics and/or bioavailability of parent drugs. These prodrugs may be activated by P450 and/or other enzymes enriched in the liver. Compared with McGuigan's prodrugs, bioavailability of the prodrugs disclosed herein can be further improved because the monocarboxylic acid or its salt intermediate generated from hydrolysis of ester of prodrug herein is stable and can be delivered into the tissues or cells by monocarboxylate transporters.

The prodrugs disclosed herein can be used for the treatment of diseases that the corresponding parent drugs are used for.

The prodrugs disclosed herein may also be used for the treatment of diseases resistant to the corresponding parent drugs.

In one aspect, the present invention provides a method of enhancing bioavailability and/or liver-targeting property of an alcohol drug, comprising protecting at least one of the hydroxyl groups of said alcohol-containing drug with a phosphoramidate moiety of formula:

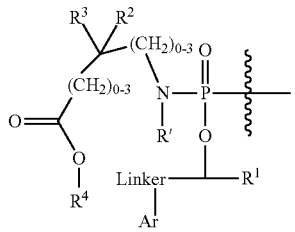

wherein:
R', $R^1$, $R^2$, and $R^3$ are each independently selected from the group consisting of hydrogen and substituted or unsubstituted alkyl, aryl, alkynyl, alkenyl, cycloalkyl, heterocyclyl, and heteroaryl groups, wherein the heterocyclyl and heteroaryl group each comprises one to three heteroatoms independently selected from O, S, and N, or, alternatively, $R^2$ and $R^3$ together with the carbon atom to which they are attached form an optionally substituted 3- to 8-, preferably 3- to 6-, membered ring;
$R^4$ is selected from the group consisting of hydrogen and substituted or unsubstituted alkyl, aryl, alkynyl, alkenyl, cycloalkyl, heterocyclyl, and heteroaryl groups, metal ions, and ammonium ions;
Ar is optionally substituted $C_6$-$C_{10}$ aryl or optionally substituted 5- to 10-membered heteroaryl comprising one to three heteroatoms independently selected from O, S, and N; and
the "linker" is selected from a bond and optionally substituted $C_1$-$C_3$ alkylene, vinyl, ethynyl, arylene and heteroarylene, wherein the heteroaryl comprises one to three heteroatoms independently selected from O, S, and N. In a preferred embodiment, alcohol-containing drug is a nucleoside, acyclonucleoside, or C-nucleoside. In a preferred embodiment, Ar is substituted aryl, in particular, 2-methylphenyl group.

In one embodiment, the present invention provides a compound of formula I:

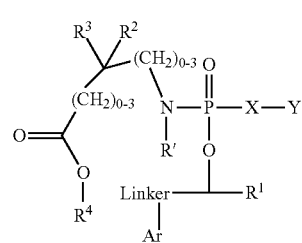

or a pharmaceutically acceptable prodrug, salt, solvate, or stereoisomer thereof, wherein:
X is oxygen (O) or methylene (—$CH_2$—);
Y is a nucleoside, acyclonucleoside, C-nucleoside, or other alcohol-containing drug molecule moiety;
R', $R^1$, $R^2$, and $R^3$ are independently selected from the group consisting of hydrogen and substituted and unsubstituted alkyl, aryl, alkynyl, alkenyl, cycloalkyl, heterocyclyl, and heteroaryl groups, wherein the heterocyclyl and heteroaryl group each comprises one to three heteroatoms independently selected from O, S, and N, or alternatively $R^2$ and $R^3$ together with the carbon atom to which they are attached form an optionally substituted 3- to 8-, preferably 3- to 6-, membered ring;
$R^4$ is selected from the group consisting of hydrogen, and substituted or unsubstituted alkyl, aryl, alkynyl, alkenyl, cycloalkyl, heterocyclyl, and heteroaryl groups, metal ions, and ammonium ions;

Ar is optionally substituted aryl or heteroaryl, wherein the heteroaryl comprises one to three heteroatoms independently selected from O, S, and N, wherein said optionally substituted aryl is preferably $C_6$-$C_{10}$ aryl, in particular phenyl or naphthyl, and said optionally substituted heteroaryl is preferably a 5- to 10-membered heteroaryl; and the "linker" is selected from a bond and optionally substituted $C_1$-$C_3$ alkylene, vinyl, ethynyl, arylene and heteroarylene groups, optionally substituted vinyl, or ethynyl or aromatic or heteroaromatic moiety, wherein the heteroarylene comprises one to three heteroatoms independently selected from O, S, and N.

In one embodiment, sometimes preferably, Ar is not an unsubstituted phenyl. In a preferred embodiment, Ar is a substituted $C_6$-$C_{10}$ aryl, more preferably, 2-methylphenyl group.

In another embodiment, the present invention provides a compound of formula II:

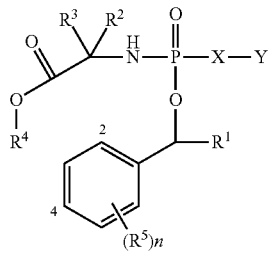

II or a pharmaceutically acceptable prodrug, salt, or solvate thereof, wherein:
$R^1$, $R^2$, $R^3$, $R^4$, X and Y are defined as above;
n is 0, 1, 2, 3, 4, or 5; and
$R^5$ at each occurrence is independently selected from halogen (F, Cl, Br, I), and substituted or unsubstituted acyloxy, acyl-NH—, $CH_3$, methoxy, alkyl, alkyloxyl, alkylamino, cycloalkyl, cycloalkyloxy, cycloalkylamino, aryl, aryloxy, arylamino, and arylalkyl. When n is 1 or 2, $R^5$ is preferably at 2 and/or 4-position(s).

In another embodiment of this aspect, Y is a nucleoside moiety comprising a sugar group and a base group.

In another embodiment of this aspect, the base group of the nucleoside moiety is selected from adenine, guanine, uracil, thymine, cytosine, and derivatives thereof.

Any amino or hydroxyl group in the Y—X moiety can be optionally protected.

In another embodiment, a compound of formula II is one or a mixture of diastereomers of formula III:

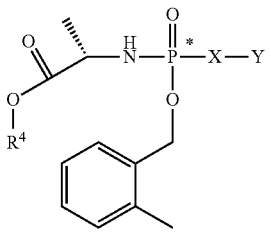

III or a pharmaceutically acceptable salt or solvate thereof, wherein $R^4$, X and Y—XH are defined as above, and wherein P* is a phosphorus atom having either R- or S-configuration.

In another embodiment, a compound of formula III is one or a mixture of diastereomers of formula IVa or IVb:

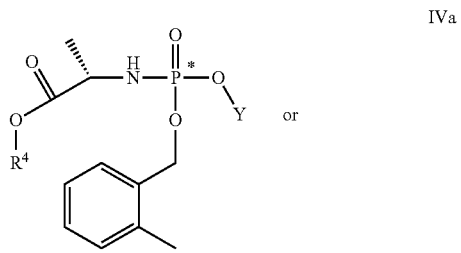

IVa or

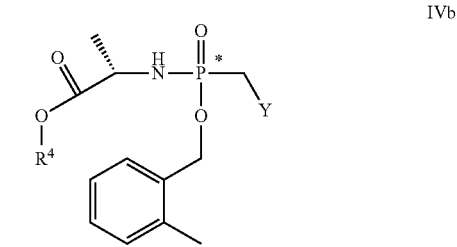

IVb or a pharmaceutically acceptable salt or solvate thereof, wherein $R^4$, Y and Y—OH are defined as above, and wherein P* is a phosphorus stereogenic center (P) having either an R- or S-configuration.

In another embodiment, the present invention provides a compound selected from the group consisting of formulas:

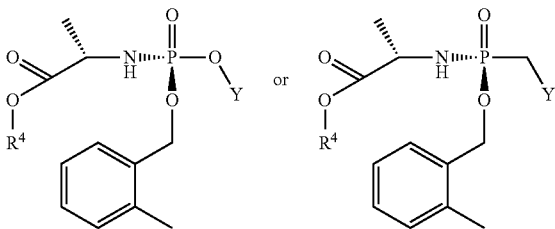

or

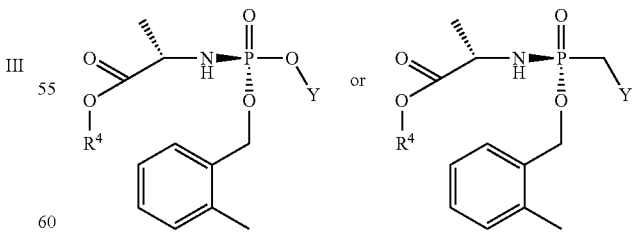

or a pharmaceutically acceptable salt or solvate thereof, wherein $R^4$, Y and Y—OH are defined as above. Preferably, the compound is diastereomerically enriched with the phosphorus stereogenic center (P) being in (R)- or (S)-configuration.

In another embodiment, the present invention provides a compound selected from the group consisting of formulas:
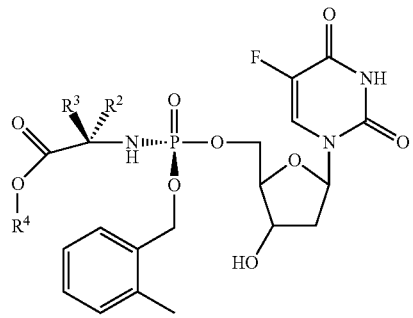
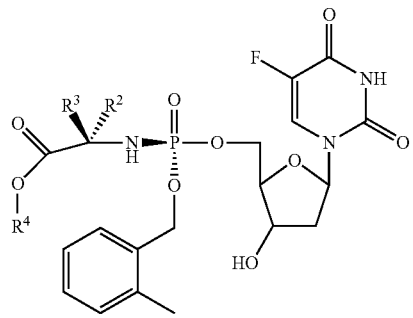
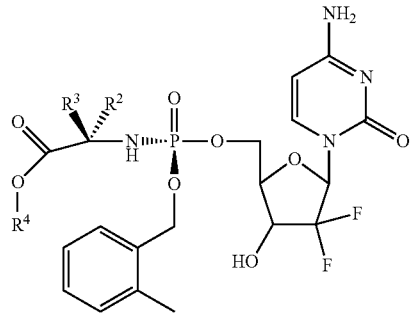
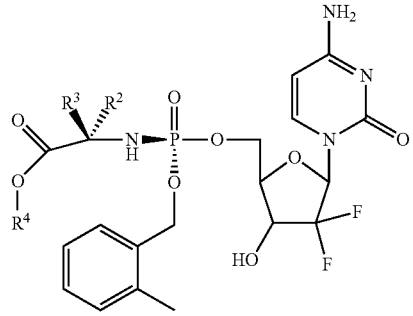
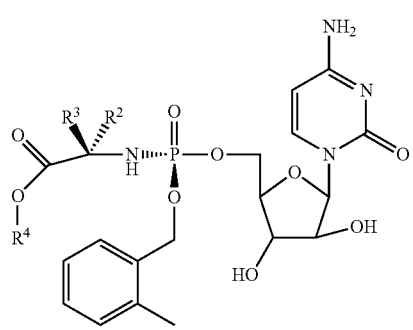
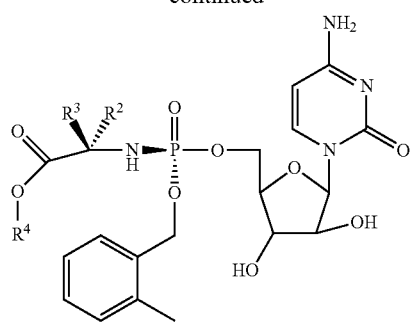
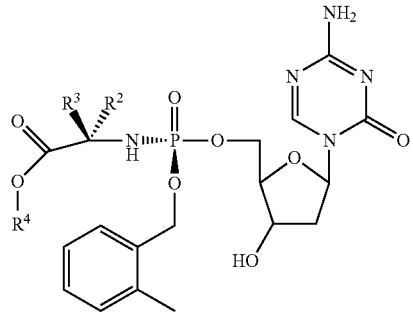
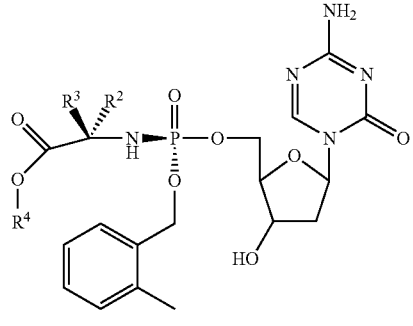
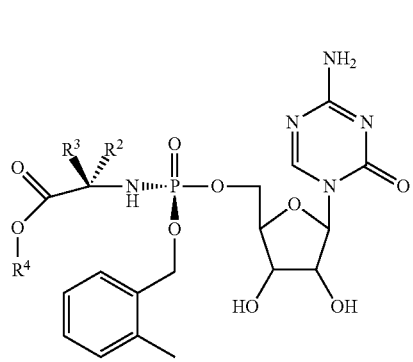
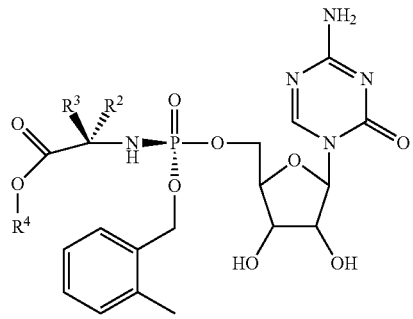

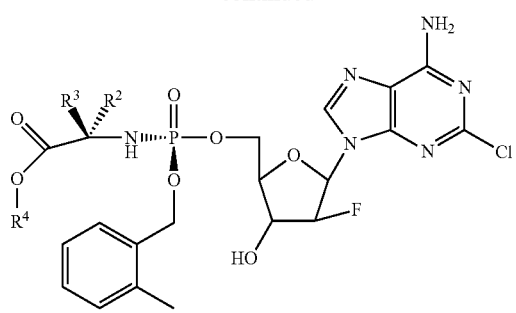
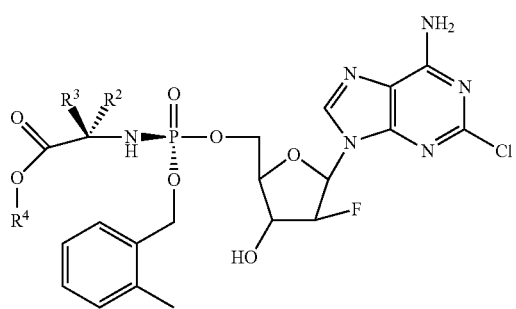
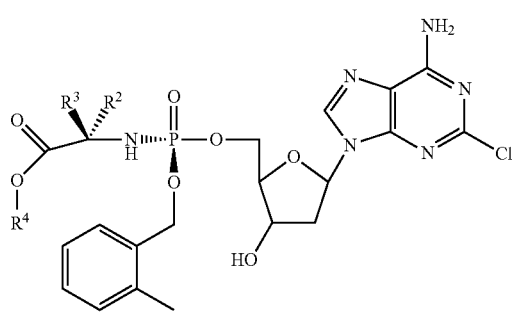
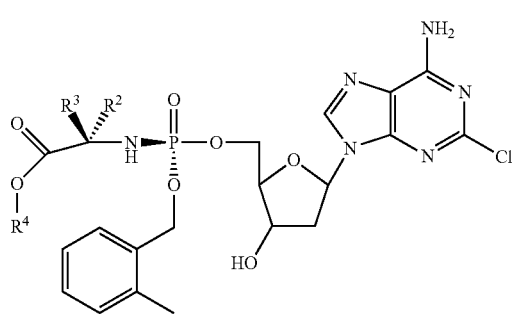
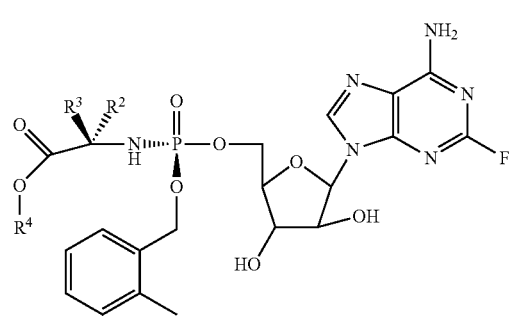
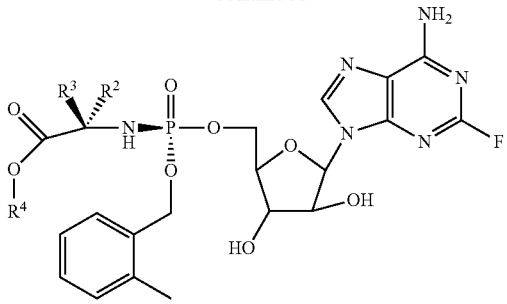
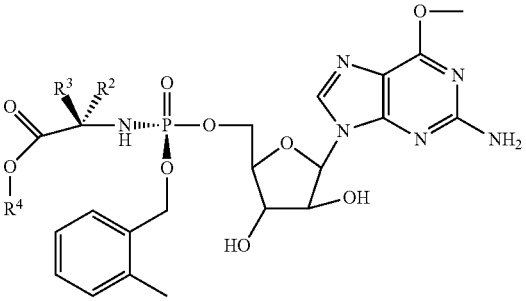
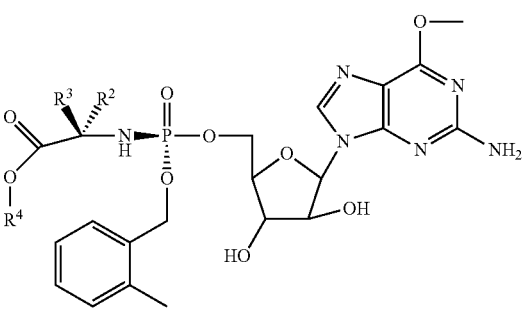
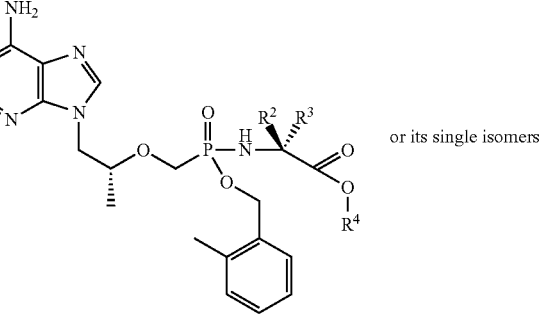
or its single isomers
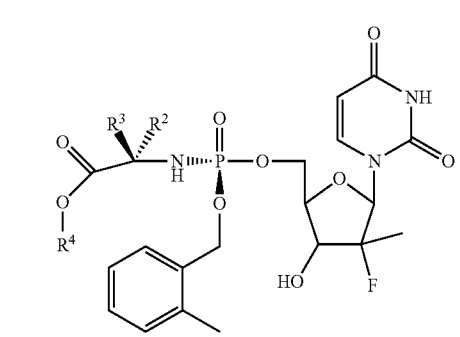

-continued
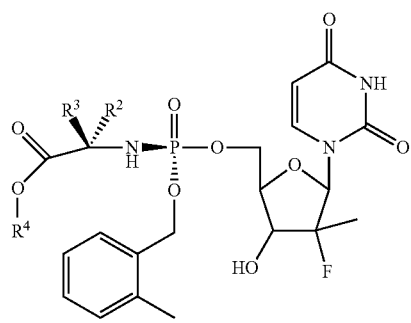
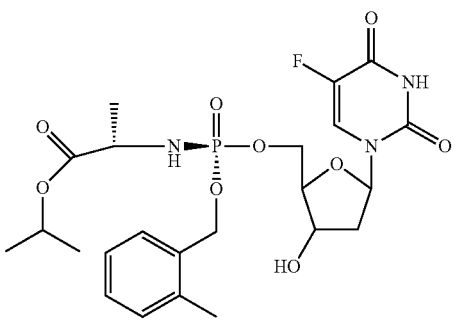
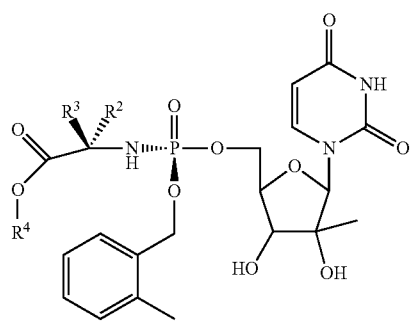
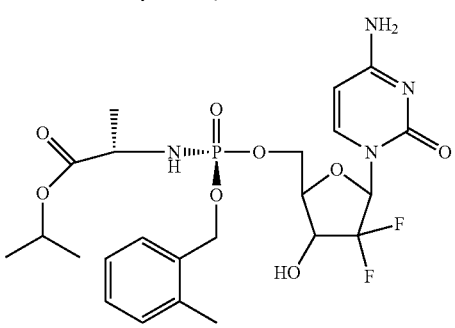
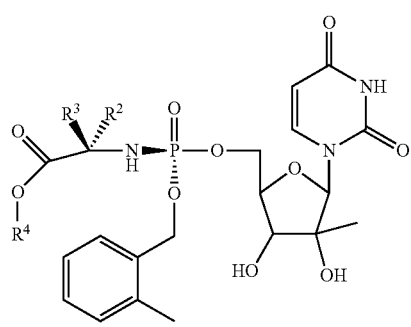
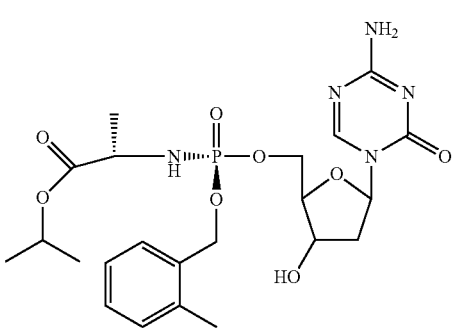
wherein $R^2$, $R^3$ and $R^4$ are defined as above. Preferably, the compound is diastereomerically enriched with the phosphorus stereogenic center (P) being in (R)- or (S)-configuration.
In another embodiment, the present invention provides a compound selected from the group consisting of formulas:
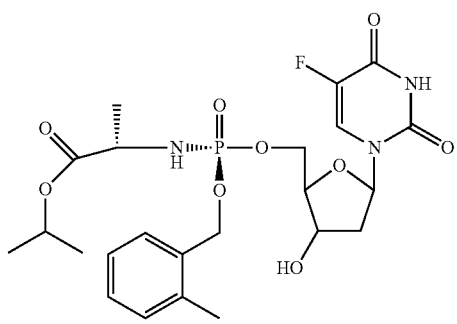
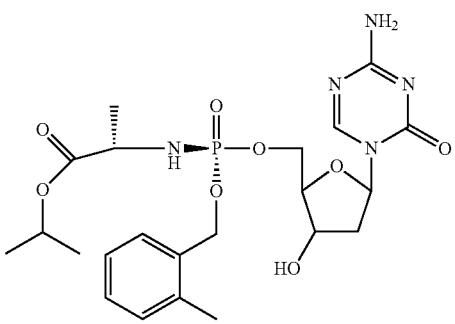

17
-continued
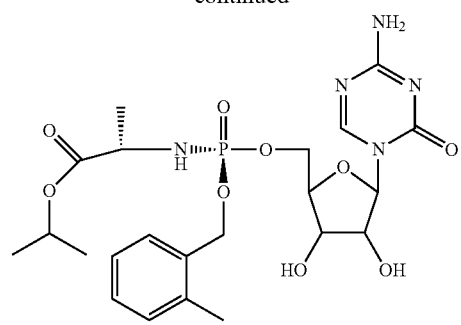
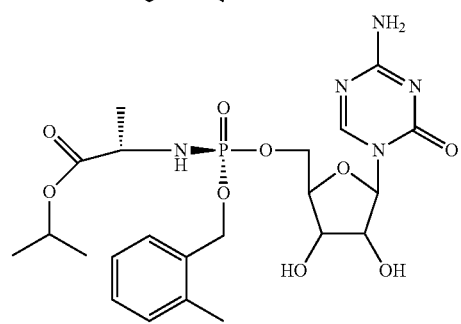
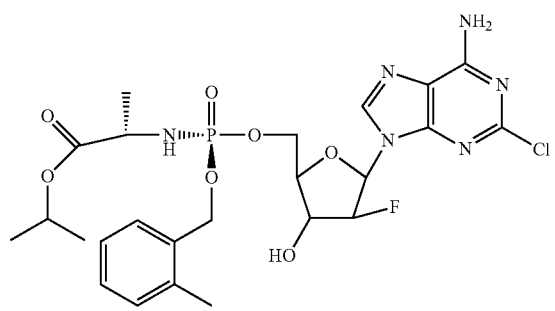
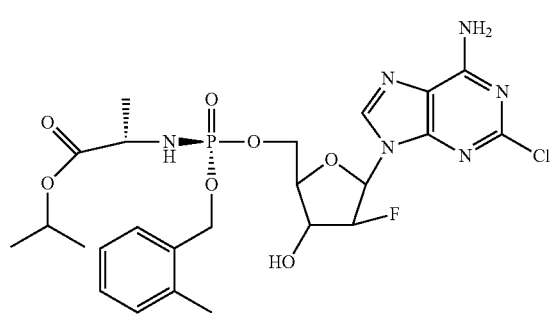
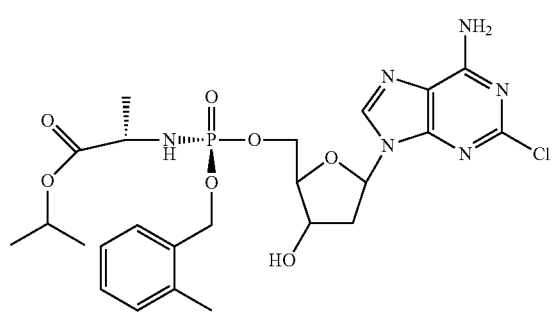
18
-continued
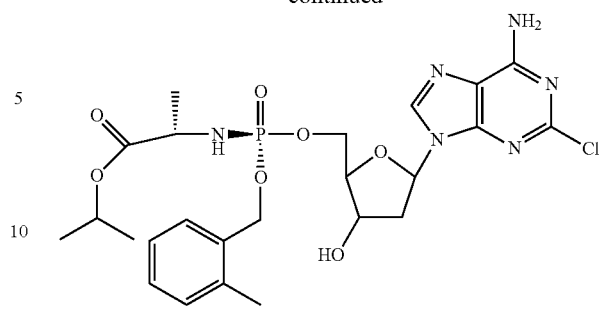
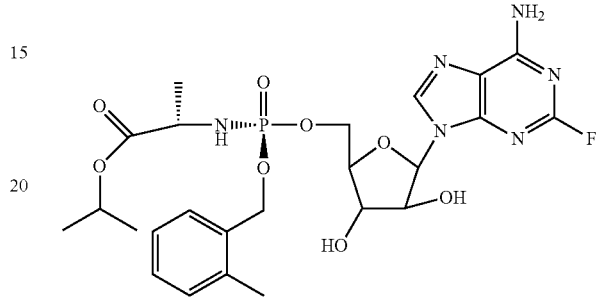
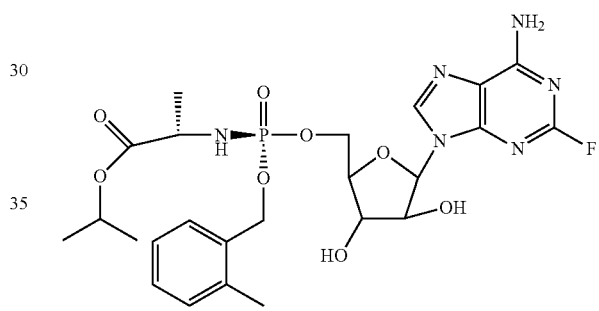
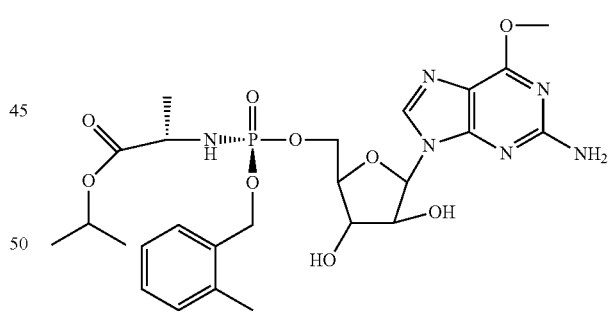
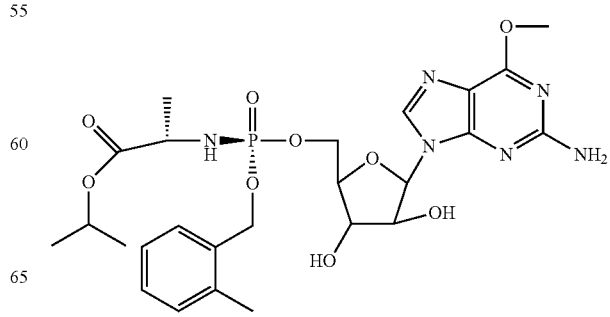

-continued

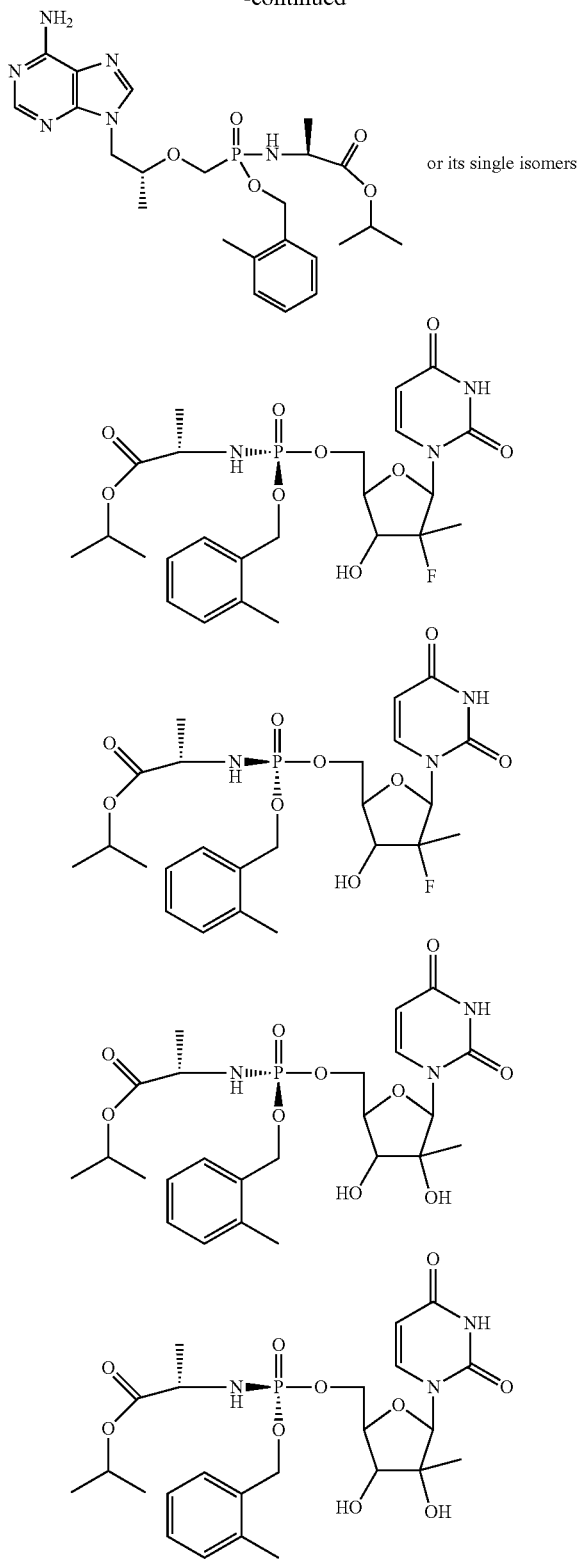

or its single isomers

In any of the above embodiments, the compound provided may comprise two diastereomers having phosphorus (P) in either (R)- or (S)-configuration. In preferred embodiments, such compound is enriched with one of such two diastereomers with phosphorus in either (R)- or (S)-configuration. In some preferred embodiments, such compound is a pure diastereomer with phosphorus (P) in only (R)-configuration, or substantially free of the corresponding "(S)-P" diastereomer. In other preferred embodiments, such compound is a pure disastereomer with phosphorus (P) in only (S)-configuration, or substantially free of the corresponding "(R)-P" diastereomer.

In one aspect, the present invention provides the compounds, or compositions thereof, for use in the treatment of a disease or disorder that is modulated or otherwise affected by liver function, in particular, hepatitis infections (e.g., HCV and HBV), liver disorders (e.g., cancers), and metabolic diseases (such as diabetes, hyperlipidemia, atherosclerosis, and obesity).

In another aspect, the prodrugs disclosed herein are prepared and used as water soluble salts, which possess useful properties different from those of any other phosphoramidate prodrugs as reported in the literature. These salts can be formed by treatment of a prodrug in carboxylic acid form with base, including organic or inorganic bases, or by hydrolysis of the ester group of a prodrug with bases. The preferred prodrug salt forms of the present invention are salts formed with cations such as $NH_4^+$, $K^+$, $Na^+$, $Ca^{2+}$, and $Mg^{2+}$. In contrast, typical McGuigan's phosphoramidate prodrugs are unstable and readily decompose to the corresponding very polar diacid after simultaneously releasing phenol under ester hydrolysis conditions.

In another aspect, the present invention provides the use of phosphoramidate and phosphonoamidate compounds as prodrugs of nucleoside, nucleotide, C-nucleoside, C-nucleotide, or other alcohol-containing drugs, or phosphonate analogs thereof, for the treatment of a variety of diseases or disorders, including, but not limited to, liver diseases or disorders. In some embodiments, the compounds of the present invention can be used in combination with other therapeutically active drug.

In another aspect, the present invention provides a pharmaceutical composition comprising any compound disclosed herein, and a pharmaceutically acceptable carrier or diluent.

In another aspect, the present invention provides a method of treating human diseases, such as viral infection or cancers, comprising administration of any compound as described herein, or a pharmaceutically acceptable prodrug thereof, to a patient in need of the treatment.

In another aspect, the present invention provides a method of treating human diseases, such as a viral infection or cancer, comprising administration of a pharmaceutical composition as described herein to a patient in need of the treatment alone or in combination with other drug(s).

In another aspect, the present invention provides the use of any compound described herein in the manufacture of medicaments for treatment of human diseases, such as viral infections or cancers.

In another aspect the present invention provides methods for manufacture of these phosphoramidate and phosphonoamidate compounds.

Based on the present disclosure, those of skill in the art will recognize that the compounds of formula I-IV can be prepared by reaction of, e.g., a hydroxyl group of the parent drug with chlorophosphoramide or chlorophosphonoamidate, for example, via condensation or dehydration.

Provided herein are also compounds, compositions and methods useful for treating hepatitis infections (HBV and HCV) and liver disorders, such as cancers, or metabolic diseases, such as diabetes, hyperlipidemia, atherosclerosis, and obesity.

Mechanisms of Activation of Phosphoramidate Prodrugs

Without intending to be bound by theory, the activation mechanism of the phosphoramidate prodrugs disclosed herein involves both esterase and P450 enzymes, through a pathway different from any phosphoramidate prodrugs reported in the literature.

Figure 2:
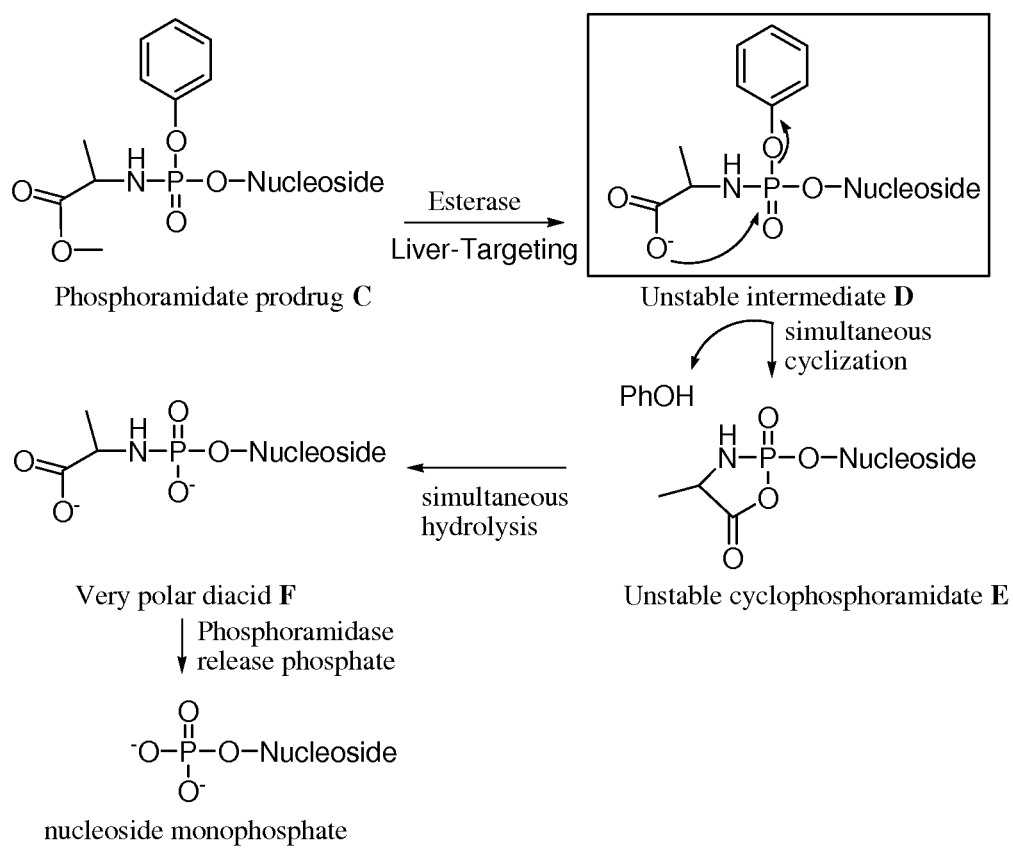
FIG. 2 illustrates mechanisms of activation of known phosphoramidate prodrugs.

Typical phosphoramidate prodrugs reported in the literature (McGuigan, et al. US 2009/0215715 A1; Sommadossi, et al. US 2009/0169504 A1; Sofia, et al. US 2010/0016251 A1; Uckun, et al. U.S. Pat. No. 7,071,176 B2; and Froehler, et al. Nucleic Acids Reseach 1988, 16, 4831; McGuigan, et al. ChemMedChem 2009, 4, 1779) are activated through similar mechanism as illustrated in FIG. 2. Ester of prodrug C is hydrolyzed to unstable intermediate D mediated by esterases. The latter simultaneously cyclizes to release phenol to form unstable cyclophosphoramidate E which is subsequently hydrolyzed to a very polar diacid F. The diacid F then releases active nucleoside monophosphate by phosphoramidase. Esterases in the intestine also can degrade the prodrug to diacid F, which may be too polar to readily pass through intestine wall and result in low bioavailability. The ester of phosphoramidate prodrug of nucleoside has demonstrated excellent stability in human plasma and instability in human liver S9, which demonstrated its liver-targeting property (J. Med. Chem. 2010, 53, 7202).

Figure 3:
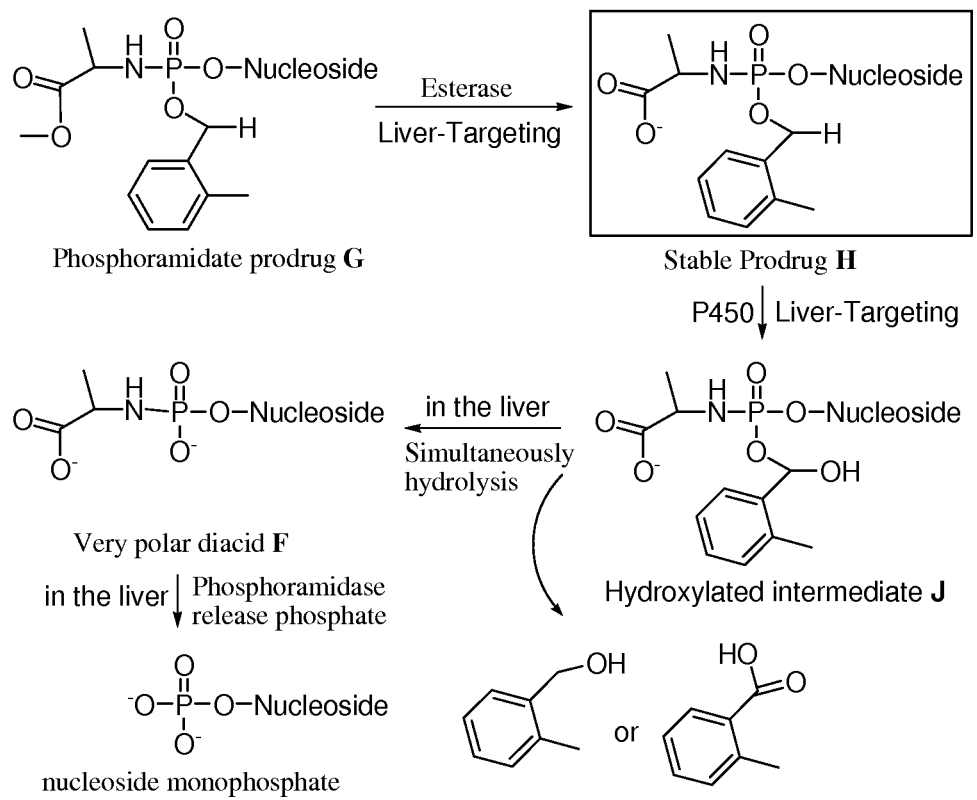
FIG. 3 illustrates proposed mechanisms of activation of phosphoramidate prodrugs according to one embodiment of the present invention.

The phosphoramidate prodrugs disclosed herein may be activated through different mechanistic pathway involving both esterase and P450 enzymes (Erion, M. et al U.S. Pat. No. 7,303,739 and references cited therein). The ester group of benzylic phosphoramidate prodrug G is hydrolyzed by esterase enriched in the liver to provide stable prodrug H and trapped in the liver (FIG. 3), which demonstrated its liver-targeting property. Again, potentially the ester group can also be hydrolyzed in intestine. However, compound H is much less polar than diacid F and can be transported into the liver by monocarboxylate transporter. Intermediate prodrug H is then metabolized by P450 to the hydroxylated intermediate J, which simultaneously releases benaldehyde to generate diacid F. Similarly, the diacid F is then metabolized to active nucleoside monophosphate. The released benzaldehyde is then metabolized to benzyl alcohol or benzoic acid. Since P450 is also highly enriched in the liver, the activation of benzylic position of the prodrug also demonstrated liver-targeting property. Therefore, the prodrugs disclosed herein have first demonstrated double-liver-targeting nature.

The phosphoramidate prodrug disclosed herein also can be prepared and used in a stable salt form of intermediate prodrug H for injectable formulation, whereas intermediates at the same stage from other phosphoramidate prodrugs reported in the literature and patent applications are unstable and decompose to a very polar diacid after simultaneously releasing phenol.

Definitions

All chemical terms used herein, unless otherwise defined, take their ordinary meanings as understood by a person of ordinary skill in the art, while certain terms are defined as follows.

The term "alkyl", as used herein, refers to a saturated straight or branched hydrocarbon radical of typically $C_1$ to $C_{20}$, preferably $C_1$ to $C_6$, and specifically includes methyl, $CF_3$, $CCl_3$, $CFCl_2$, $CF_2Cl$, ethyl, $CH_2CF_3$, $CF_2CF_3$, propyl, isopropyl, cyclopropyl, and the like. Non-limiting examples of moieties with which the alkyl group can be substituted are selected from the group consisting of halogen (fluoro, chloro, bromo or iodo), hydroxyl, amino, alkylamino, arylamino, alkoxy, aryloxy, nitro, cyano and the like.

"Alkenyl" includes monovalent olefinic unsaturated hydrocarbon groups, in certain embodiment, having up to 11 carbon atoms, which can be straight-chained or branched, and having at least 1 or 2 sites of olefinic unsaturation (i.e., C=C bond). Exemplary alkenyl groups include ethenyl or vinyl (—CH=CH$_2$), allyl (—CH$_2$CH=CH$_2$), isopropenyl (—C(CH$_3$)=CH$_2$), and substituted vinyl, or the like.

"Alkynyl" includes acetylenic unsaturated hydrocarbon groups, in certain embodiments, having up to about 11 carbon atoms, which can be straight-chained or branched and having at least 1 or 2 sites of alkynyl unsaturation (i.e., CC bond). Non-limiting examples of alkynyl groups include acetylenic, ethynyl, propargyl, and the like.

The term "aryl", as used herein, includes phenyl, biphenyl, or naphthyl, and preferably phenyl. The term includes both substituted and unsubstituted moieties. The aryl group can be substituted with any described moiety, including, but not limited to, one or more moieties selected from the group consisting of halogen (fluoro, chloro, bromo or iodo), alkyl, hydroxyl, amino, alkylamino, arylamino, alkoxy, aryloxy, nitro, cyano, sulfono, sulfato, phosphono, phosphato, or phosphonoxy, either unprotected, or protected as necessary.

"Cyclic alkyl" or "cycloalkyl" includes 3-7 membered rings of hydrocarbon, such as cyclopropyl, cyclopentyl, cyclohexyl, etc., all optionally substituted.

"Heteroaromatic group" or "heteroaryl" refers to a aromatic ring radical which consists of carbon atoms and from one to five, preferably one to three, heteroatoms independently selected from the group consisting of nitrogen, oxygen and sulfur. For purposes of this invention, the heteroaryl radical may be a monocyclic or bicyclic and preferably 5- to 10-membered. Examples include, but are not limited to, furanyl, isothiazolyl, imidazolyl, indolyl, indazolyl, isoindolyl, isoxazolyl, oxadiazolyl, oxazolyl, purinyl, pyrrolyl, pyrazolyl, pyridinyl, pyrazinyl, pyrimidinyl, pyridazinyl, quinazolinyl, quinolinyl, isoquinolinyl, thiazolyl, thiadiazolyl, triazolyl, tetrazolyl, triazinyl, thiophenyl, benzimidazolyl, benzothiazolyl, benzothiadiazolyl, benzoxazolyl, benzofuranyl, benzothienyl, and benzotriazolyl.

Unless otherwise specified, as used herein, the term "heterocyclyl" is intended to mean a 3- to 10-membered monocyclic or bicyclic, heterocyclic non-aromatic group which consists of carbon atoms and from 1 to 3 heteroatoms independently selected from the group consisting of N, O and S. Examples of such heterocyclyl radicals include, but are not limited to, piperidinyl, piperazinyl, pyrrolidinyl, tetrahydrofuranyl, tetrahydropyranyl, decahydroisoquinolyl, imidazolinyl, imidazolidinyl, isothiazolidinyl, isoxazolidinyl, morpholinyl, octahydroindolyl, oxazolidinyl, 4-piperidonyl, pyrazolidinyl, thiazolidinyl, or the like.

When any group, in particular, alkyl, alkenyl, "cycloalkyl," "aryl," "heterocyclyl," or "heteroaryl", is said to be "optionally substituted," it means that the group is or is not substituted by from one to five, preferably one to three, substituents independently selected from halogen, $C_1$-$C_6$ alkyl, $C_1$-$C_6$ alkoxy, $C_1$-$C_6$ haloalkyl, $C_1$-$C_6$ haloalkoxy, hydroxy, oxo, $C_1$-$C_7$ acyl, cyano, nitro, and amino group, or the like. When the phrase "optionally substituted" is used before a list of groups, it means that each one of the groups listed may be substituted.

"Alkoxy or alkyloxy" includes the group —OR where R is alkyl.

"Amino" includes the radical —NH$_2$.

The term "alkylamino" or "arylamino" includes an amino group that has one or two alkyl or aryl substituents, respectively.

"Halogen" or "halo" includes chloro (Cl), bromo (Br), fluoro (F) or iodo (I).

"Monoalkylamino" includes the group alkyl-NHR'—, wherein R' is selected from alkyl or aryl.

"Alkylthio" and "arylthio" refer to the group —SR, where R is alkyl or aryl, respectively.

The term "protected", as used herein and unless otherwise defined, refers to a group that is added to an oxygen, nitrogen, or phosphorus atom to prevent its further reaction or for other purposes. A wide variety of oxygen and nitrogen protecting groups are known to those skilled in the art of organic synthesis. In any of the structures disclosed or described herein, in particular, nucleosides or nucleotides, any hydroxyl or amino groups can be either protected or unprotected. When a hydroxyl or amino group is called to be "protected," it means that the group is protected by a removable group, such as acyl, phosphonyl, phosphate, or the like, as understood by a person of skill in the art. Suitable protecting groups for prodrugs are preferably hydrolysable under physiological conditions in vivo.

The term "nucleoside" includes natural or modified nucleoside, acyclic nucleoside and C-nucleoside.

The term "C-nucleoside" referred to nucleoside in which glycosyl bond is attached to carbon on modified nucleic bases instead of nitrogen in normal nucleoside (see reference for C-nucleoside review: Chemistry of Nucleosides and Nucleotides by Leroy B Townsend 1994, Science, Chapter 5 The Chemistry of C-nucleosides, Kyoichi A Watanabe pp 421). C-nucleoside is not limited to compound cited in the review.

"Pharmaceutically acceptable salt" includes any salt of a compound provided herein which retains its biological properties and which is not toxic or otherwise undesirable for pharmaceutical use.

The term "prodrug" as used herein refers to any compound that generates a biologically active compound when administered to a biological system as the result of spontaneous chemical reaction(s), enzyme catalyzed reactions(s), and/or metabolic process(es) or a combination of each. Standard prodrugs are formed using groups attached to functionality, e.g. —OH, —$NH_2$, associated with the drug, that cleave in vivo. The prodrugs described in the present invention are exemplary, but not limited to, and one skilled in the art could prepare other known varieties of prodrugs.

The term "L-nucleoside" refers to enantiomer of the natural and modified β-D-nucleoside analogs.

The term "arabinofuranosyl nucleoside" refers to nucleoside analogues containing an arabinofuranosyl sugar, i.e. where the 2'-hydroxyl of ribofuranosyl sugars of natural (normal) nucleoside is on the opposite face of the sugar ring.

The term "dioxolane sugar" refers to sugars that contain an oxygen atom in place of the 3' carbon of the ribofuranosyl sugar.

The term "fluorinated sugars" refers to sugars that have 1-3 fluorine atoms attached to sugar carbons.

The term "nucleoside" refers to a purine or pyrimidine base, or analogs thereof, connected to a sugar, including heterocyclic and carbocyclic analogues thereof.

The term "therapeutically effective amount" refers to an amount that has any beneficial effect in treating a disease or condition.

The term "phosphate" refers to —O—$PO_3^{2-}$.

The term "phosphoramidate" refers to —N—$PO_3$.

The term "phosphonate" refers to —CHR—$PO_3^{2-}$.

As used herein, a "nucleoside phosphoramidate or phosphonoamidate as a therapeutic agent" includes a nucleoside (including acyclonucleoside and C-nucleoside) therapeutic agent derivatized to a phosphoramidate and phosphonoamidate having a benzyl group containing one or more substituents selected from, but not limited to, amino, $C_1$-$C_{20}$ acyloxy, $C_1$-$C_{20}$ alkyl, aryl, $C_1$-$C_{20}$ alkyloxy, aryloxy or aralkyloxy group, all optionally substituted. The therapeutic agent is, for example, an antiviral agent that includes, or has been derivatized to include, a reactive group, such as a hydroxyl, for attachment of the phosphoramidate or phosphonoamidate moiety. Such therapeutic agents include, but are not limited to, nucleosides, nucleoside analogs including acyclonucleosides, C-nucleosides, and alcohol-containing drugs. In some embodiments, phosphoramidates of nucleoside and nucleotide analogues are also provided, such as phosphoramidates of 1'-, 2'-, 3'- and 4'-branched or disubstituted nucleosides. Such compounds can be administered in a therapeutically effective amount for the treatment of infectious diseases, liver disorders, including cancers and infectious diseases, such as hepatitis B and hepatitis C infections, including resistant strains thereof. On occasions, the phosphoramidate or phosphonoamidate prodrugs of present invention may also generally be referred to as "phosphate prodrugs" in this application, which meanings should be well understood by a person of skill in the art by taking into consideration the context in which such references are made.

The term "parent drug" refers to nucleosides, acyclonucleoside and their mono-phosphate drugs (Y—O—$PO_3^{2-}$).

The term "parent drug" also refers to phosphonate-containing drugs [Y—$CH_2$—P(O)(OH)$_2$].

The term "biologically active drug or agent" refers to the chemical entity that produces the biological effect. In this invention, biologically active agents refer to nucleoside (Y—OH), nucleoside mono-phosphates (Y—O—$PO_3^{2-}$), nucleoside diphosphates (Y—O—$P_2O_6^{3-}$), nucleoside triphosphates (Y—O—$P_3O_9^{4-}$), nucleoside phosphonate [Y—$CH_2$P(O)(OH)$_2$, Y—$CH_2PO_3^{2-}$], non-nucleoside phosphonate, monophosphate (Y—$CH_2P_2O_6^{3-}$) or its diphosphate (Y—$CH_2P_3O_9^{4-}$), alcohol-containing compound.

The term "alkaryl" or "alkylaryl" includes an aryl group with an alkyl substituent. The term aralkyl or arylalkyl includes an alkyl group with an aryl substituent.

The term "purine" or "pyrimidine" base includes, but is not limited to, adenine, $N^6$-alkyl-6-aminopurines, $N^6$-acyl-6-aminopurines (wherein acyl is C(O)(alkyl, aryl, alkylaryl, or arylalkyl), $N^6$-benzyl-6-aminopurine, $N^6$-vinyl-6-aminopurine, $N^6$-ethynyl-6-aminopurine, 6-cycloaminopurine, 7-deazapurine, modified 7-deazapurine, thymine, cytosine, $N^4$-acylcytosine, 5-fluorocytosine, 5-methylcytosine, 6-azacytosine, uracil, 5-fluorouracil, 5-alkyluracil, 5-vinylpyrimidine, 5-ethynyluracil, 5-hydroxymethyluracil, 5-amidouracil, 5-cyanouracil, 5-iodouracil, 5-Br-vinyluracil, 5-azacytosine, 5-azauracil, triazolopyridine, imidazolopyridine, pyrrolopyrimidinyl, and pyrazolopyrimidinyl. Purine bases include, but are not limited to, guanine, adenine, 2-fluoroadenine, 2-chloroadenine, hypoxanthine, 7-deazaguanine, 7-deazaadenine, 2,6-diaminopurine, and 6-chloropurine, 6-alkoxypurine, 6-deoxyguanine, 6-alkylthiopurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term "acyl" or "O-linked ester" includes a group of the formula —C(O)R', wherein R' is a straight, branched, or cyclic alkyl or aryl.

The term "amino acid" includes naturally occurring and synthetic α-, β-, γ- or δ-amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration. Alternatively, the amino acid can be a derivative of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. "Diastereomerically enriched diastereomer" means that the material contains greater than 80% of major diastereomer and less than 20% of minor diastereomer, in particular with regard to (R)- and (S)-configurations of the phosphorus stereogenic center in the phosphoramidate and phosphonoamidate prodrugs.

"Solvate" includes a compound provided herein or a salt thereof that further includes a stoichiometric or non-stoichiometric amount of solvent bound by non-covalent intermolecular forces. Where the solvent is water, the solvate is a hydrate.

As used herein, the term "moiety" refers to a partial structure of a molecule, often a significant portion of a molecule retaining characteristic features of the molecule. In some instances, it is exchangeable with the term "group" or "substituent." To illustrate, a "sugar moiety" means a sugar group attached to a structure of interest by a covalent bond through an oxygen atom of the sugar molecule after losing a hydrogen atom from a hydroxyl group or through a carbon atom after losing a hydroxyl group from the carbon atom.

The phrases "substituted or unsubstituted", "optionally substituted", or the like, are used before or after a list of groups or substituents, they modify every one of the groups or substitutents that can take substituents, while excluding those that cannot.

As used herein, the terms "subject" and "patient" are used interchangeably. The terms "subject" refers to an animal, such as a mammal including a non-primate (e.g., cow, pig, horse, cat, dog, rat, and mouse) and a primate (e.g., a monkey such as a cynomolgus monkey, a chimpanzee). In one embodiment, the subject is a human.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound provided herein. In one embodiment, a therapeutic agent is an agent which is known to be useful for, or has been or is currently being used for the treatment or prevention of a disorder or one or more symptoms thereof.

"Therapeutically effective amount" includes an amount of a compound or composition that, when administered to a subject for treating a disease, is sufficient to effect such treatment for the disease. A "therapeutically effective amount" can vary depending on, inter alia, the compound, the disease and its severity, and the age, weight, etc of the subject to be treated.

"Treating" or "treatment" of any disease or disorder refers, in one embodiment, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder.

Parent Drugs Suitable for Prodrug Derivatization of the Present Invention

Various kinds of parent drugs can benefit from the prodrug methodologies of the present invention. It is preferred that the prodrug protecting group be attached to a hydroxyl group on the parent drug. In many cases the parent drug may have many such functional groups. The preferred group selected for attachment of the prodrug is the one that is most important for biological activity and is chemically suitable for attachment to the prodrug. Thus, the phosphoric prodrug moiety will prevent the prodrug from having biological activity. An inactive prodrug should reduce systemic side effects because higher drug concentrations will be in the target organ (liver) relative to non-hepatic tissues.

There are a number of classes of therapeutically useful drugs (including nucleoside or non-nucleoside) containing hydroxyl functional group which can be used to be derivatized to phosphoramidate or phosphonoamidate prodrugs of the present invention. These compounds include nucleoside, C-nucleoside, nucleotide, phosphonate and other alcohol-containing compounds. Prodrugs disclosed herein derivatized from these compounds are considered to fall within the scope of the present invention.

Some illustrative, non-limiting examples of such compounds are described below.

One class of exemplary nucleoside drugs (D- and L-) that are therapeutically useful and can be derivatized to form prodrugs of the present invention is a compound (Y—OH) of formula V:

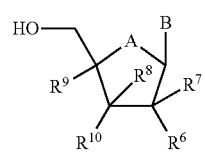

wherein:
"A" is selected from, but not limited to, O, S, $CH_2$, CHF, $C=CH_2$, $C=CHF$, and $CF_2$;
$R^6$ and $R^7$ are selected independently from, but are not limited to, H, OH, $CH_3O$, F, Cl, Br, I, CN, $N_3$, methyl, ethyl, vinyl, ethynyl, chlorovinyl, fluoromethyl, difluoromethyl, and trifluoromethyl, or alternatively $R^6$ and $R^7$ together form a vinylidene group

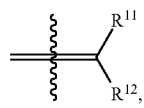

wherein $R^{11}$ and $R^{12}$ are independently selected from hydrogen, halogen (F, Cl, Br, and I), methyl, CN, and $N_3$;
$R^8$ is selected from but is not limited to, H, methyl, ethyl, vinyl, ethynyl, chlorovinyl, fluoromethyl, difluoromethyl, and trifluoromethyl;

$R^9$ is selected from but is not limited to, H, CN, $N_3$, methyl, ethyl, vinyl, ethynyl, chlorovinyl, fluoromethyl, difluoromethyl, and trifluoromethyl;

$R^{10}$ is selected from, but is not limited to, H, OH, F, cyano, and azido.

B is selected from, but is not limited to, pyrimidine and purine and derivatives thereof selected from formulas B-1 and B-2:

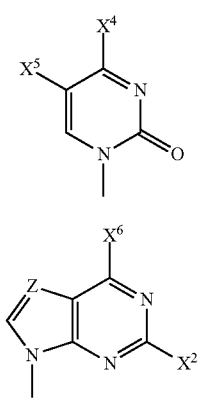

wherein $X^2$ is selected from, but not limited to, H, $NH_2$, NHMe, $NMe_2$, and halogen (I, Br, Cl, F);

$X^4$ is $NH_2$ or OH;

$X^5$ is selected from, but not limited to, halogen (I, Br, Cl, F), OH, $NH_2$, methyl, vinyl, alkyl, 2-bromovinyl, and ethynyl;

$X^6$ is selected from, but not limited to, H, OH, and optionally substituted alkyloxy (preferably OMe and OEt,), aryloxy, cyclic alkyloxy, alkylthio (preferably SMe and SEt), arylthio, cyclic alkylthio, thienyl, furyl, alkylamino, dialkylamino, arylamino, arylalkylamino, cyclic alkylamino, and cyclopropylamino;

Z is Nitrogen (N) or $CX^7$; and $X^7$ is selected from, but not limited to, H, and optionally substituted vinyl, ethynyl, and halogen (I, Br, Cl, F);

wherein any amino and hydroxyl groups in the above structures are optionally protected.

Other modified pyrimidines or purines, such as 5-azapyrimidine, 6-azapyrimidine, 3-deazapyridine, 3-fluoro-3-deazapyrimidine, and 8-aza-7-deazapurine, and modified bases for C-nucleoside, or the like, are also considered to fall within the scope of the present invention.

Another class of exemplary nucleoside drugs (D- and L-) therapeutically useful and suitable to be derivatized to prodrugs of the present invention is selected from compounds of formula VI:

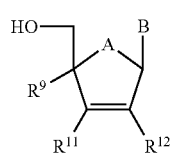

wherein B, A, and $R^9$ are defined as above;

$R^{11}$ and $R^{12}$ are independently selected from, but are not limited to, H, $N_3$, F, CN, and optionally substituted alkyl (preferably methyl) and vinyl.

Other classes of parent drugs suitable for the prodrug derivatization of the present invention include compounds of formulas (D- and L-isomers) VII and VIII:

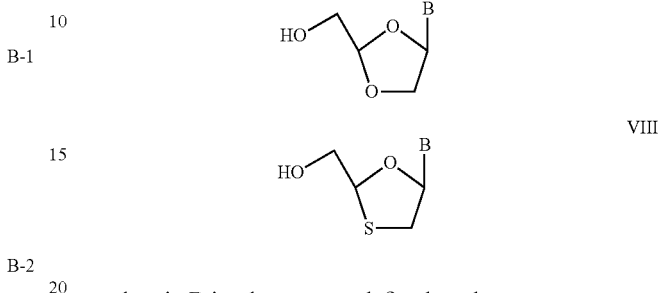

wherein B is a base group defined as above.

Another class of parent drugs suitable for the prodrug modification of the present invention is selected from, but is not limited to, nucleoside phosphonates (Biochem. Pharmacol. 2007, 73, 911, which is hereby incorporated by reference).

Another class of parent drugs suitable for the prodrug derivatization of the present invention is selected from acyclic nucleosides, including, but not limited to, acyclovir, ganciclovir and pencyclovir.

Another class of parent drug suitable for the prodrug derivatization of the present invention is selected from C-nucleosides, a special class of nucleosides (see reference for C-nucleoside review: Chemistry of Nucleosides and Nucleotides by Leroy B Townsend 1994, Science, Chapter 5, The Chemistry of C-nucleosides, Kyoichi A Watanabe, p. 421, which is hereby incorporated by reference). C-Nucleosides suitable for the present invention include, but are not limited to, the compounds cited in the review.

When some of nucleosides are not good substrates for kinases and show no biological activity while their nucleotides or nucleoside monophosphates are biologically active, the parent drugs are referred to the corresponding nucleoside monophosphates.

Preferably, compounds suitable for prodrug derivatization herein include, but are not limited to, nucleosides (including prodrugs thereof) of formulas described in Table 1.

TABLE 1

| Examples of parent nucleosides |
|---|

Gemcitabine

TABLE 1-continued

Examples of parent nucleosides

Cytarabine

Decitabine

Floxuridine

Clofarabine

Cladribine

Fludarabine
MP: monophosphate

Nelarabine

BVDU

Azacitidine

Entecavir

TABLE 1-continued
Examples of parent nucleosides
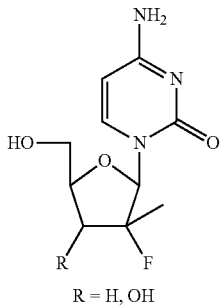
R = H, OH
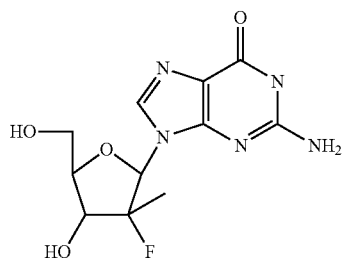 [SMILES: CC1(F)C(O)C(CO)OC1n1cnc2c(=O)[nH]c(N)nc21]
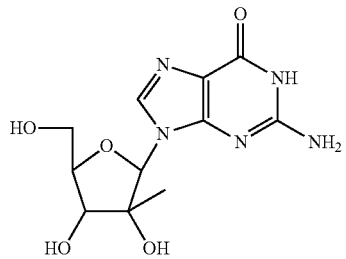 [SMILES: CC1(O)C(O)C(CO)OC1n1cnc2c(=O)[nH]c(N)nc21]
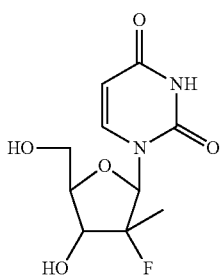 [SMILES: CC1(F)C(O)C(CO)OC1n1ccc(=O)[nH]c1=O]
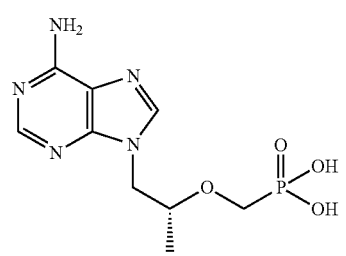
Tenofovir
TABLE 1-continued
Examples of parent nucleosides
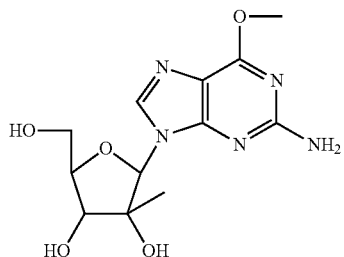 [SMILES: COc1nc(N)nc2c1ncn2C1OC(CO)C(O)C1(C)O]
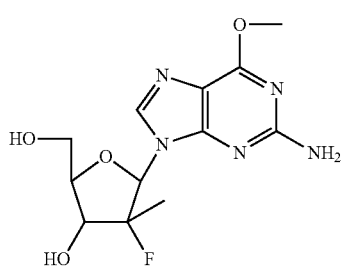 [SMILES: COc1nc(N)nc2c1ncn2C1OC(CO)C(O)C1(C)F]
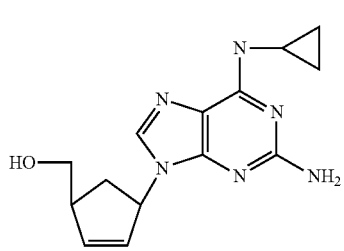 [SMILES: Nc1nc(NC2CC2)c2ncn(C3C=CC(CO)C3)c2n1]
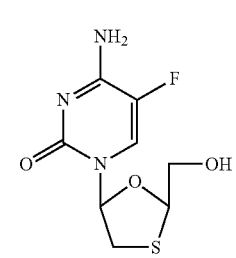 [SMILES: Nc1nc(=O)n(C2CSC(CO)O2)cc1F]
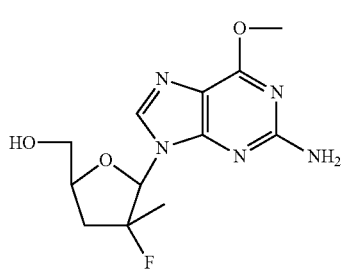 [SMILES: COc1nc(N)nc2c1ncn2C1OC(CO)CC1(C)F]
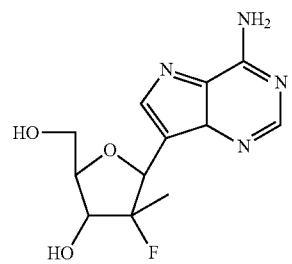 [SMILES: CC1(F)C(C2=CN=C3C(N)=NC=NC23)OC(CO)C1O]

TABLE 1-continued

Examples of parent nucleosides

[Chemical structure: nucleoside with 4-aminopyrrolopyrimidine base, ribose with 2'-F and 2'-methyl]

[Chemical structure: cytosine with thiolane sugar - emtricitabine-like]

[Chemical structure: uridine with 2'-methyl, 2'-hydroxy ribose]

Prodrugs derivatized from alcohol-containing drugs by disclosed technologies herein are also considered to fall within the scope of the present invention.

Therapeutic Use

Therapeutic use of the prodrugs herein is provided for the treatment of viral infections, cancers and other liver disorders. These prodrugs can be used to improve bioavailability and/or pharmacokinetics of parent drugs. These prodrugs and compositions disclosed herein can be administered either alone or in combination with other therapeutically effective agents.

In one unique aspect, prodrugs disclosed herein can be prepared and used as water soluble salts. The water solubility is a useful property different from any other phosphoramidate prodrugs reported in the literature. Therefore, the prodrug technology provided herein is more versatile and useful than the phosphoramidate technologies reported in the literature.

The phosphoramidate and phosphonoamidate compounds of a variety of therapeutic agents disclosed herein can be used for the treatment of such diseases that the corresponding parent drugs are used for.

In some embodiments, the prodrugs disclosed herein can also be used for the treatment of viruses resistant to parent drugs.

Such phosphoramidate and phosphonoamidate compounds can advantageously enhance drug delivery to the liver. In some embodiments, the compounds permit delivery of an active 5'-monophosphate of a nucleoside to the liver, which can enhance the formation of active triphosphorylated compound.

In one embodiment, the present invention provides methods for the treatment of liver disorders, the methods comprising the administration of an effective amount of a compound provided herein, or a pharmaceutically acceptable salt thereof to an individual host. In certain embodiments, the methods encompass the step of administering to the subject in need thereof an amount of a compound effective for the treatment of liver disorders in combination with other agent(s) effective for the treatment of the diseases. The compound can be any compound as described herein, and the other agent can be any agent(s) known to those of skill in the art.

Prodrug technologies of the present invention can be applied in conversion of a large number of inactive nucleosides into prodrugs of therapeutically useful nucleotides.

Thus, the phosphoramidate prodrugs disclosed herein for all alcohol-containing drugs are considered to fall within the scope of the present invention.

Therapeutic use of the prodrugs disclosed herein is also provided for the treatment of hepatitis infections (including HBV and HCV) and liver disorders including liver cancer and metabolic diseases, such as diabetes, hyperlipidemia, atherosclerosis, and obesity.

Dosage and Administration

Another embodiment of the present invention is directed to a composition comprising a compound selected from compounds of formulae I, II, III, IVa and IVb, or pharmaceutically acceptable salts (acid or basic addition salts) and solvates (preferably hydrates) thereof, and a pharmaceutically acceptable medium selected from excipients, carriers, diluents, and equivalent media.

It is contemplated that the formulation of the above embodiment can contain any of the compounds of formulae I, II, III, IVa, IVb and those exemplified herein, either alone or in combination with another compound of the present invention.

The compounds of the present invention may be formulated in a wide variety of oral administration dosage forms and carriers. Oral administration dosage forms include, but are not limited to, tablets, coated tablets, hard and soft gelatin capsules, solutions, emulsions, syrups, or suspensions. Compounds of the present invention are efficacious when administered by suppository administration, among other routes of administration. The most convenient manner of administration is generally oral using a convenient daily dosing regimen that can be adjusted according to the severity of the disease and the patient's response to the antiviral or anticancer medication.

A compound or compounds of the present invention, as well as their pharmaceutically acceptable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as suspensions, emulsions, or filled capsules for oral use; or in the form of suppositories for rectal or vaginal administration. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the desired dose and pharmacokinetic parameters.

The term "excipient", as used herein, refers to a compound that is used to prepare a pharmaceutical composition, and is generally safe, non-toxic and neither biologically nor otherwise undesirable, and includes excipients that are acceptable for human pharmaceutical use. The compounds of this invention can be administered alone but will generally be administered in admixture with one or more suitable pharmaceutical excipients, diluents or carriers selected with regard to the intended route of administration and standard pharmaceutical practice.

Solid form preparations include powders, tablets, pills, capsules, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs and aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

Suitable formulations along with pharmaceutical carriers, diluents and excipients are described in Remington: The Science and Practice of Pharmacy 1995, edited by E. W. Martin, Mack Publishing Company, 19th edition, Easton, Pa., which is hereby incorporated by reference. The compounds of the present invention can also be encapsulated in liposomes, such as those disclosed in U.S. Pat. Nos. 6,180,134, 5,192,549, 5,376,380, 6,060,080, and 6,132,763, each of which is incorporated by reference. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (e.g., salt formulation), which are well within the ordinary skill in the art. It is also well within the ordinary skill of the art to modify the route of administration and dosage regimen of a particular compound in order to manage the pharmacokinetics of the present compounds for maximum beneficial effect in patients.

Preparation of Compounds

The compounds provided herein can be prepared, isolated or obtained by any method apparent to those of skill in the art based on the present disclosure. Exemplary methods of preparation are described in detail in the Examples Section below.

An exemplary preparation of reagents for phosphoramidates is illustrated in Scheme 1. Treatment of phosphorus oxychloride (1 eq. POCl$_3$) with a solution of triethylamine (1 eq.) and 2-methylbenzyl alcohol (1, 1 eq.) at −78° C. gave dichloride 2, which was treated with isopropyl L-alanyl ester hydrochloride (1 eq.) then triethylamine (2 eq.) to afford monochlorophosphoramidate 3, which was used for the reaction with nucleoside without purification for the preparation of phosphoramidate prodrugs as diastereomeric mixture. Reaction of compound 3 with pentafluorophenol (1 mol eq.) and triethylamine (1 mol eq.) provided diastereomerically enriched reagent 4 after recrystallization of a mixture of diastereomers.

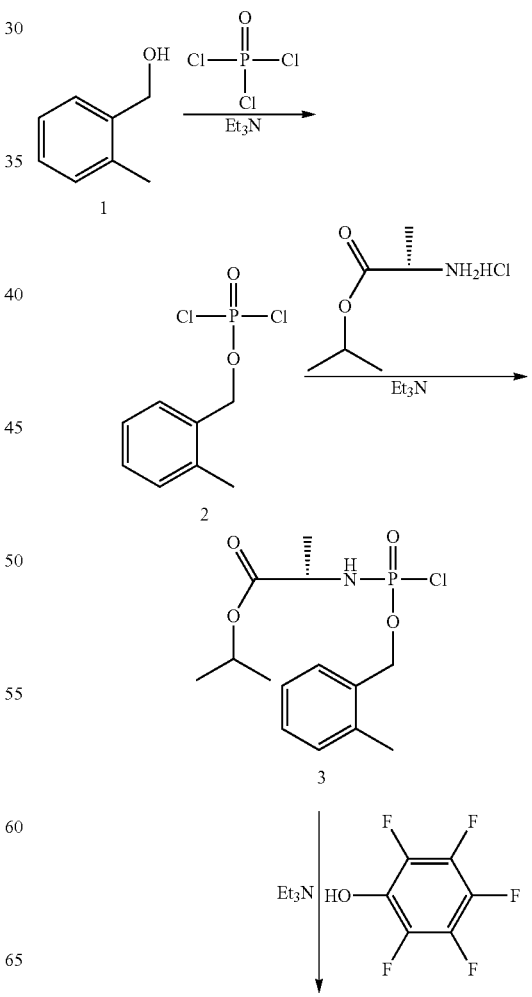

Scheme 1. Preparation of reagents for phosphoramidates

Preparation of the Phosphoramidate Prodrug as a Diastereomeric Mixture

Treatment of nucleoside (FDUR as example) with phosphoramidate monochloride 3 in the presence of N-methylimidazole (NMI) produced target compound 5 (Scheme 2).

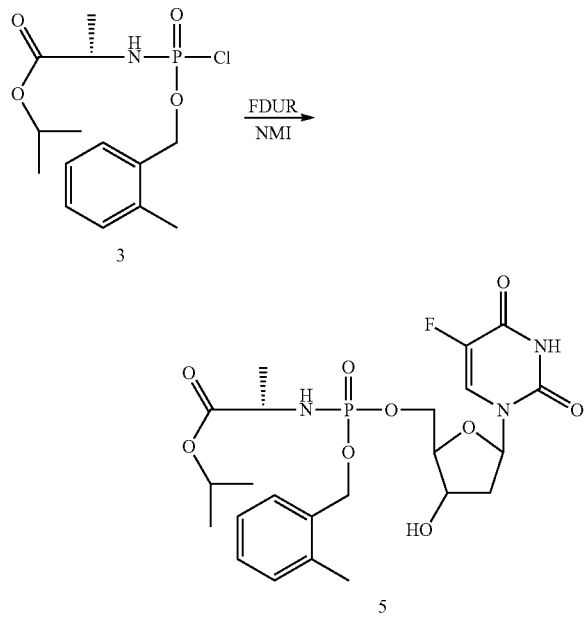

For the asymmetric synthesis of diastereomerically enriched phosphoramidate prodrugs, Ross et al (WO 2011/123668 A2) recently disclosed method for preparation of McGuigan's prodrug and IDX-prodrug. A diastereomerically enriched phosphorus reagent (Ross-reagent) can be obtained by recrystallization from the mixture of diastereomers prepared by general method. Reaction of the chiral reagent with nucleoside in the presence of base, such as t-BuMgCl, produced diastereomerically enriched phosphoramidate prodrug (Ross-prodrug in Scheme 3):

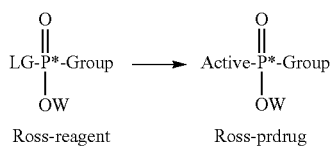

wherein "Active" is a nucleoside or drug moiety; "Group" is an amine moiety or S-containing moiety for IDX-prodrug or aminoacid residue; W is an aryl group (preferably phenyl and naphthyl), or —$(CH_2)_n SC(O)C(CH_3)_m(CH_2OH)$ wherein n' is 2 or 3 and m' is 0, 1, 2, or 3; and LG is a leaving group.

However, no benzylic analogs were reported or prepared in WO 2011/123668.

The present inventors surprisedly discovered that diastereomerically enriched benzylic phosphoramidate reagent 4 could also be prepared by recrystallization from a mixture of diastereomers (Scheme 1). Treatment of 3'-OTBS-protected FDUR (3'-OTBS-Floxuridine) with the chiral benzylic phosphoramidate 4 in the presence of base, t-BuMgCl, gave diastereomerically enriched phosphoramidate 6. Phosphoramidate ester prodrug F5 was obtained by deprotection of 6 with tetrabutylammonium fluoride (TBAF). A phosphoramidate prodrug in sodium salt form (7) was also prepared by the treatment of compound F5 with 1N NaOH (Scheme 4).

To the knowledge of the present inventors, this is the first time that a phosphoramidate prodrug in salt form was prepared by taking advantage of better stability of benzylic phosphoramidate prodrugs over phenyl or naphthyl phosphoramidate prodrugs (Scheme 4).

Scheme 4. Preparation of chiral phosphoramidate and its salt

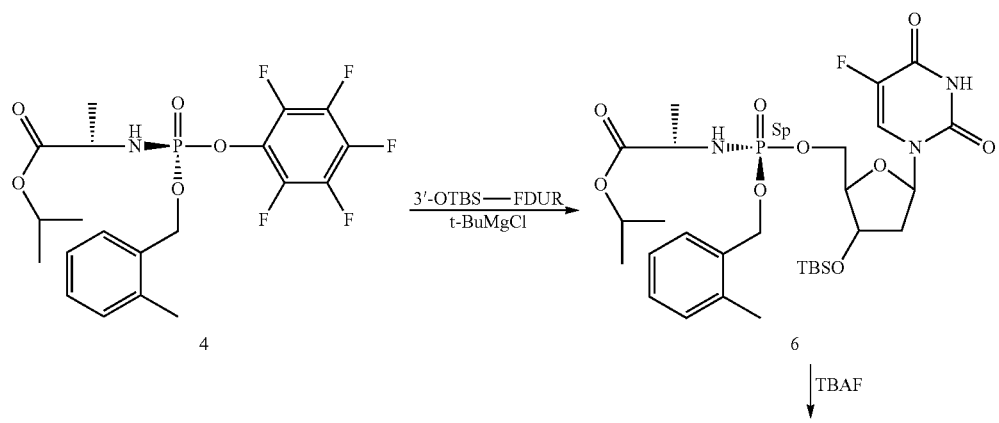

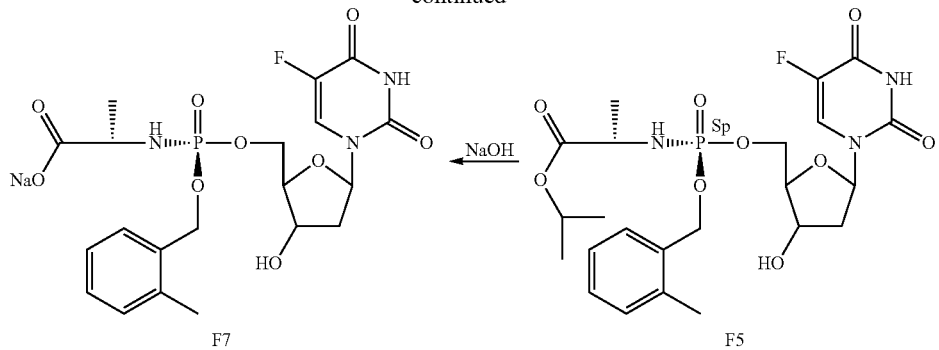

The chiral chemistry of benzylic phosphoramidate reagents and phosphoramidate prodrugs has been assigned analogously according to the disclosure of Ross et al.

Similarly, prodrugs of other nucleosides or nucleotides can be prepared by those of skill in the art based on the present disclosure.

Biological Evaluation

Anticancer activity assay. The compounds synthesized as anti-cancer agents can each be tested in leukaemic cell lines to assess their anticancer efficacy. The compounds can be tested using the MTS assay reagents from Promega (CellTiter96 Aqueous One solution proliferation assay). Such testings can be done by a person of ordinary skill in the art following the common testing procedures as described in the literature. For example, the compounds can be tested at 5 µM concentration (see, e.g., WO 2006/100439).

Anti-Hepatitis C Activity. Anti-HCV activity and cytotoxicity of compounds disclosed herein were assayed following the method described in WO 2007/027248.

Anti-HBV assay. Compounds of the present invention can be assayed for anti-HBV activity according to any assay known to those of skill in the art.

Compounds can be assayed for accumulation of active metabolites in liver cells of a subject according to any assay known to those of skill in the art. In certain embodiments, liver cells of the subject can be used to assay for the liver accumulation of the compound(s) or derivatives thereof, e.g., a nucleoside, nucleoside phosphate or nucleoside triphosphate derivative thereof.

Compounds can be assayed for accumulation of active metabolites in the liver of animals according to any assay known to those of skill in the art.

EXAMPLES

The following Examples illustrate the synthesis of representative compounds provided herein. These examples are not intended, nor are they to be construed, as limiting the scope of the claimed subject matter. Numerous modifications and variations of the subject matter are possible in view of the teachings herein and, therefore, are within the scope of the claimed subject matter. $^1$H-NMR is recorded on Varian 400 MHz. The chiral chemistry was assigned based on patent application (Ross et al WO 2011/123668 A2).

Example 1

Preparation of Phosphoramidate Monochloride 3

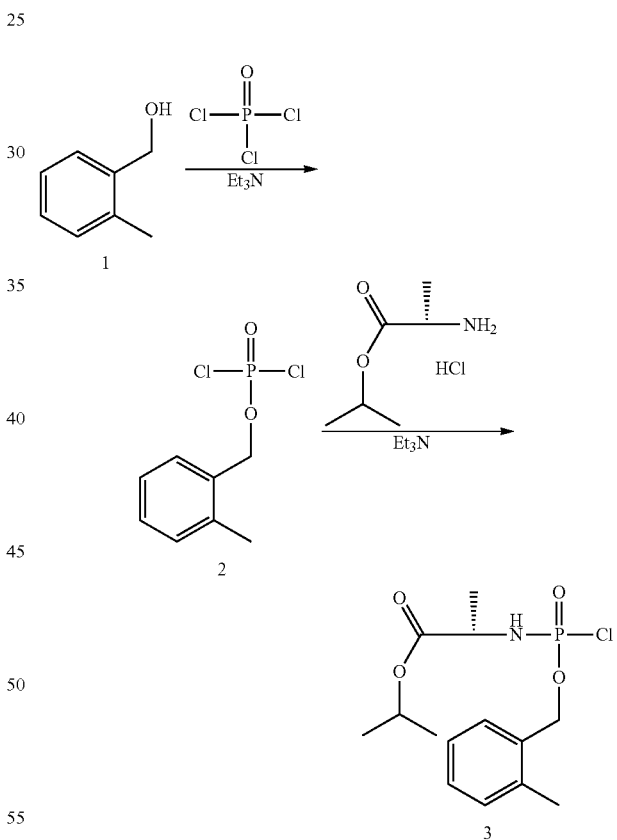

To a solution of phosphorus oxychloride (3.07 g, 20 mmol) in THF (40 mL) was added a solution of 2-methylbenzyl alcohol (1, 2.44 g, 20 mmol) and triethylamine (2.02 g, 20 mmol) in THF (10 mL) at −78° C. and the mixture was stirred at −78° C. for 3 h. To the resulting mixture was added L-alanyl isopropyl ester hydrochloride (3.35 g, 20 mmol) and then triethylamine (4.04 g, 40 mmol) in THF (10 mL) at −78° C. and the mixture was stirred at −78° C. for 1 h then room temperature for overnight to give a reaction mixture of crude compound 3.

Example 2

Similarly, benzyl phosphoramidate monochloride 3' was prepared.

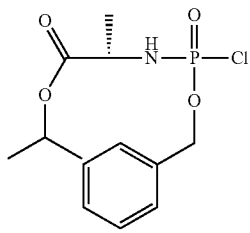

3'

Example 3

Preparation of Chiral Reagent 4 as a Diastereomerically Enriched Isomer

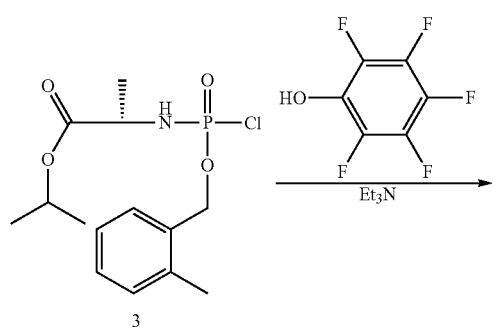

A mixture of compound 3 was prepared as in Example 1 in 20 mmol scale. To the mixture was added a solution of pentafluorophenol (20 mmol) and triethylamine (20 mmol). To the mixture was added an additional triethylamine (20 mmol) and the mixture was stirred at room temperature for 4 h. EtOAc (200 mL) was added and the mixture was washed with water and brine and dried over $Na_2SO_4$. Solvent was removed and the residue was purified by silica gel column chromatography (5-50% EtOAc in hexane) to give crude compound as a mixture of diastereomers. $^1$H-NMR (CDCl$_3$): δ 7.18-7.36 (m, 4H), 5.23 (dd, J=7.2 Hz, 1H), 5.02 (m, 1H), 4.00 (m, 1H), 3.76 (m, 1H), 2.38, 2.37 (ss, 3H), 1.42, 1.37 (d, J=7.2 Hz, 2H), 1.24 (m, 9H). Recrystallization of the mixture of diastereomers from EtOAc-hexane gave diastereomerically enriched reagent 4. $^1$H-NMR (CDCl$_3$): δ 7.17-7.34 (m, 4H), 5.22 (d, J=7.2 Hz, 2H), 5.00 (m, 1H), 4.00 (m, 1H), 3.73 (t, J=11.6 Hz, 1H), 2.37 (s, 3H), 1.42 (d, J=6.8 Hz, 3H), 1.21 (dd, J=6.0 Hz, 6H). LC-MS (ESI): 482 [M+1]$^+$. $^{31}$P (CDCl$_3$, 162 MHz): δ 5.69.

Example 4

Similarly, chiral benzyl phosphoramidate reagent 4' was prepared. $^1$H-NMR (CDCl$_3$): δ 7.39 (s, 5H), 5.20 (d, J=7.6 Hz, 2H), 5.01 (m, 1H), 4.01 (m, 1H), 3.75 (m, 9.6 Hz, 1H), 1.42 (d, J=6.8 Hz, 3H), 1.22 (dd, J=6.4 Hz, 6H). LC-MS (ESI): 468 [M+1]$^+$. $^{31}$P (CDCl$_3$, 162 MHz): δ 5.01.

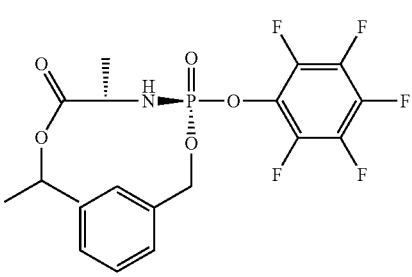

4'

Example 5

Diastereomers of 4 and 4' can also be recovered from the filtration mother liquor by chromatographic methods or any other available separation methods, respectively.

Example 6

Preparation of Phosphoramidate Prodrug 5 as a Diastereomeric Mixture

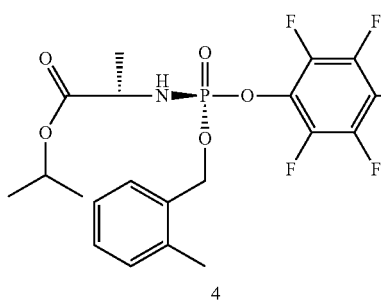

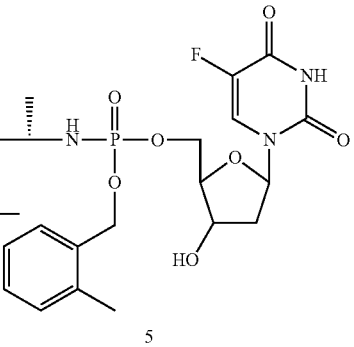

5

For using crude compound 3 for the direct reaction with nucleoside without purification, THF of the reaction mixture of crude 3 from Example 1 was removed and the residue was filtered and washed with ethyl ether (50 mL). The filtrate and washing was evaporated to give crude 3 which was dissolved in CH$_2$Cl$_2$ (10 mL) for the next reaction without further purification. To a suspension of nucleoside (FDUR, 246 mg, 1 mmol) in CH$_2$Cl$_2$ (10 mL) was added N-methylimidazole (1 mL) and the solution was cooled in an ice-bath. To the cooled solution was added a solution of crude 3 (1 mL, maximum 2 mmol) and the resulting solution was stirred in an ice-bath for 3 h. Water (5 mL) was added and the mixture was extracted with EtOAc (2×200 mL). The organic solution was washed with 0.5 N HCl solution, aq NaHCO$_3$, brine, and dried over Na$_2$SO$_4$. The solvent was concentrated to dryness and the residue was purified by silica gel chromatography (0-8% MeOH in CH$_2$Cl$_2$) to give compound 5 as a mixture of diastereomers (350 mg, 64%). LC-MS (ESI): 554 [M+1]$^+$.

Example 7

Preparation of intermediate 3'-O-(t-butyldimethylsilyl)-5-fluoro-2'-deoxyuridine (3'-OTBS-FDUR)

To a solution of 5-fluoro-2'-deoxyuridine (FDUR) (4.92 g, 20 mmol) in pyridine (100 mL) was added DMTrCl (10.16 g, 30 mmol) portion-wise at 0° C. and the solution was stirred at 0° C. for 2 h. Water (5 mL) was added and the mixture was evaporated to dryness and the residue was co-evaporated with toluene (2×20 mL). The residue was dissolved in EtOAc (200 mL) and the solution was washed with brine and dried over Na$_2$SO$_4$. Solvent was removed and the residue was dissolved in CH$_2$Cl$_2$ (100 ml). To the solution were added imidazole (4.08 g, 60 mmol) then t-butyldimethylsilylchloride (TBSCl, 4.52 g, 30 mmol) and the mixture was stirred at room temperature for overnight. Water (50 mL) was added and the mixture was evaporated to dryness. The residue was dissolved in EtOAc (300 mL) and the solution was washed with brine and dried over Na$_2$SO$_4$. Solvent was removed and the residue was co-evaporated with toluene twice then dissolved in CH$_2$Cl$_2$ (200 mL). To the solution was added trifluoroacid (TFA, 3 mL) and the solution was stirred at room temperature for 3 h. Water (5 mL) was added and the mixture was stirred for 30 min then methanol (10 mL) added. After 10 min, the solution was neutralized with 30% ammonium hydroxide. The mixture was concentrated to dryness and the residue was purified by silica gel chromatography to give product as solid (5.6 g, 78%). $^1$H-NMR (CDCl$_3$): δ 8.88 (br s, 1H), 7.96 (d, J=6.4 Hz, 1H), 6.23 (m, 1H), 4.78 (m, 1H), 3.95 (m, 1H), 3.79 (m, 1H), 2.28 (m, 2H), 0.88 (s, 9H), 0.00, 0.09 (ss, 6H). LC-MS (ESI): 361 [M+1]$^+$.

Example 8

Preparation of Chiral Compound 6

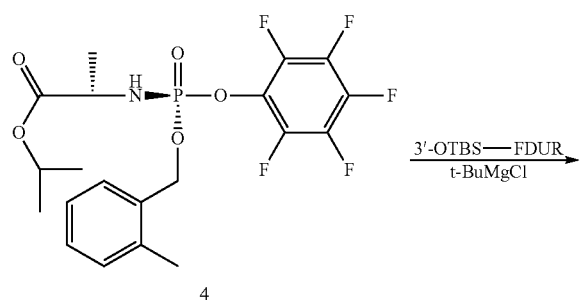

4

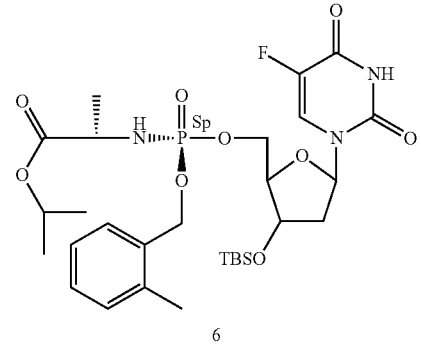

6

To a solution of 3'-O-TBS-5-fluoro-2'-deoxyuridine (3'-OTBS-FDUR, 1.44 g, 4 mmol) and compound 4 (2.89 g, 6 mmol) in THF (100 mL) was added t-BuMgCl (1M, 8.8 mmol, 8.8 mL) slowly at room temperature, and the reaction mixture was stirred at room temperature for 1 h. EtOAc (200 mL) was added and the mixture was washed with brine and dried over Na$_2$SO$_4$. Solvent was removed and the residue was purified by silica gel column chromatography (0-5% MeOH in CH$_2$Cl$_2$) to give compound 6 as a foam (2.5 g, 95%). $^1$H-NMR (CDCl$_3$): δ 7.78 (d, J=6.4 Hz, 1H), 7.26 (m, 4H), 6.24 (m, 1H), 5.10 (m, 2H), 5.00 (m, 1H), 4.41 (m, 1H), 4.16 (m, 2H), 4.01 (m, 1H), 3.86 (m, 1H), 3.44 (m, 1H), 2.36 (s, 3H), 2.29 (m, 1H), 1.99 (m, 1H), 1.32 (d, J=7.2 Hz, 3H), 1.23 (dd, J=6.4 Hz, 6H), 0.87 (s, (H), 0.00, 0.04 (ss, 6H). LC-MS (ESI): 658 [M+1]$^+$. $^{31}$P (CDCl$_3$, 162 MHz): δ 8.96.

Example 9

Preparation of Chiral Ester Prodrug F5 (FDURPAE)

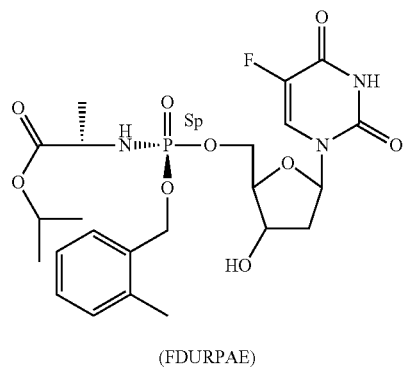

(FDURPAE)

To a solution of compound 6 (2.0 g, 3.04 mmol) in THF (50 mL) was added tetrabutylammonium fluoride (TBAF, 1M in THF, 4.5 mmol, 4.5 mL) and the solution was stirred at room temperature for 3 h. Solvent was removed and the residue was purified by silica gel column (0-5% MeOH in CH$_2$Cl$_2$) to give compound F5 (1.5 g, 92%) as white foam. $^1$H-NMR (CDCl$_3$):

δ 9.20 (Br S, 1H), 7.70 (d, J=6.4 Hz, 1H), 7.20 (m, 4H), 6.20 (t, J=5.6 Hz, 1H), 5.11 (m, 2H), 5.01 (m, 1H), 4.47 (m, 1H), 4.23 (m, 2H), 3.81 (m, 2H), 2.43 (m, 1H), 2.37 (s, 3H), 2.16 (m, 1H), 1.31 (d, J=6.8 Hz, 3H), 1.22 (dd, J=6.4 Hz, 6H). $^{31}$P (CDCl$_3$, 162 MHz): δ 9.45.

Example 10

Preparation of Chiral Ester Prodrug F7 (FDURPAN) as Sodium Salt

To a solution of compound F5 (1.5 g, 2.76 mmol) in THF (50 mL) was added aqueous NaOH (1N, 5.52 mmol) slowly and the solution was stirred at room temperature for 16 h. EtOAc (5 mL) was added and the mixture was evaporated to dryness. The residue was triturated with Et$_2$O and the solid was dried to give compound F7. $^1$H-NMR (CD$_3$OD): δ 7.53 (d, J=9.6 Hz, 1H), 7.25 (d, J=7.6 Hz, 1H), 7.07 (m, 3H), 6.19 (m, 1H), 5.00 (d, J=6.8 Hz, 2H), 4.28 (m, 1H), 4.08 (m, 2H), 3.89 (m, 1H), 3.53 (m, 1H), 2.25 (s, 3H), 2.15 (m, 1H), 1.92 (m, 1H), 1.19 (d, J=6.8 Hz, 3H). $^{31}$P-NMR (CD$_3$OD): δ 10.30.

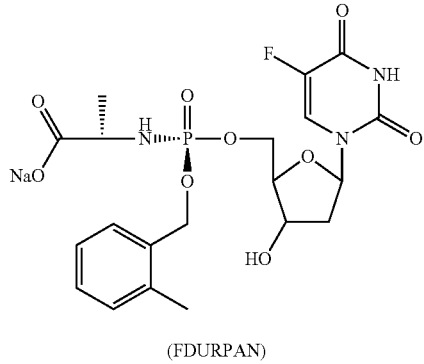

(FDURPAN)

Example 11

By following the above procedure using corresponding nucleoside or reagent, the following prodrugs (Table 2) of typical nucleosides in Table 1 can be prepared.

TABLE 2

Structures of the selected prodrugs

| Structure | | [M + H]$^+$ |
|---|---|---|
| | | 544.1 |
| | | 561.1 |
| | | 525.2 |

TABLE 2-continued

Structures of the selected prodrugs

| Structure | [M + H]⁺ |
|---|---|
| | 542.2 |
| | 601.1 |
| | 583.2 |
| | 583.2 |

TABLE 2-continued

Structures of the selected prodrugs

| Structure | [M + H]⁺ |
|---|---|
| (structure of prodrug with 6-methoxy-2-fluoropurine nucleoside, isopropyl alaninate, o-tolyl phosphoramidate) | 595.2 |
| (structure of prodrug with 6-methoxy-2-fluoropurine nucleoside, isopropyl alaninate, o-tolyl phosphoramidate) or its single isomers | 505.2 |
| DGX-TFV (tenofovir prodrug with isopropyl alaninate, o-tolyl phosphonamidate) | |
| (structure of 2'-fluoro-2'-methyl uridine prodrug with isopropyl alaninate, o-tolyl phosphoramidate) | 558.2 |
| (structure of 2'-fluoro-2'-methyl uridine prodrug with isopropyl alaninate, o-tolyl phosphoramidate) | |
| (structure of 2'-methyl uridine prodrug with isopropyl alaninate, o-tolyl phosphoramidate) | 556.2 |
| (structure of 2'-methyl uridine prodrug with isopropyl alaninate, o-tolyl phosphoramidate) | |

Example 12

Preparation of DGX-TFV of Tenofovir

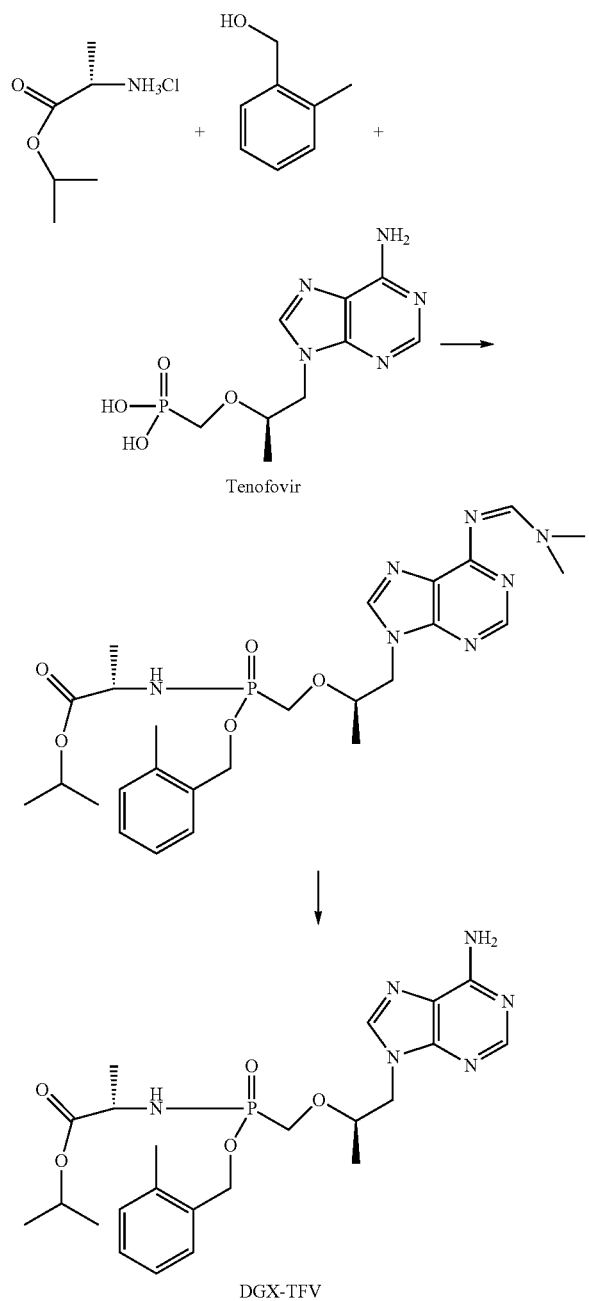

Tenofovir

DGX-TFV

To a solution of Tenofovir (1 mmol, 287 mg) in CH$_2$Cl$_2$ (10 mL) were added DMF (87.6 mg, 1.2 mmol) and then (COCl)$_2$ (444 mg, 3.5 mmol) at room temperature, and the mixture was stirred at room temperature until a solution was obtained in about 20 min. The solution was heated at 45° C. for 3 h. Solvent was removed and CH$_2$Cl$_2$ (10 mL) was added. Solvent was removed and the residue was dissolved in CH$_2$Cl$_2$ (10 mL). To the solution was added L-alanine isopropyl ester hydrochloride (211 mg, 1.2 mmol) at −78° C. To the solution was added Et$_3$N (0.34 mL, 2.5 mmol) at −78° C. and the solution was stirred at room temperature for 2 h. To the solution was added 2-methylbenzyl alcohol (183 mg, 1.5 mmol) and Et$_3$N (0.27 mL, 2 mmol) at −78° C. To the mixture was added CH$_2$Cl$_2$ (5 mL) to dilute the mixture and the mixture was stirred at room temperature for 16 h. Solvent was removed and the residue was purified by silica gel column (0-10% MeOH in CH$_2$Cl$_2$) to give N-protected intermediate (150 mg, 27%). $^1$H-NMR (CDCl$_3$, 400 MHz): δ, 9.09 (br. S, 1H), 8.56, 8.55 (ss, 1H), 8.03, 8.00 (ss, 1H), 7.32-7.14 (m, 4H), 5.05-4.88 (m, 3H), 4.43-4.30 (m, 1H), 4.02-3.57 (m, 5H), 3.28, 3.24 (6H), 3.18-3.07 (m, 2H), 1.44-1.16 (m, 18H). [M+1]$^+$560.

N-Protected intermediate was dissolved in a solution (5 mL) of a mixture of iPrOH and AcOH (30/2.3 v/v) and the solution was heated at 60° C. for 3 h. To the solution was added toluene (10 mL) and evaporated to dryness under reduced pressure to dryness. The residue was purified by silica gel column (0-10% MeOH in CH$_2$Cl$_2$) to give DGX-TFV (110 mg, 84%). $^1$H-NMR (CDCl$_3$, 400 MHz): δ, 9.098.297, 8.290 (ss, 1H), 7.91, 7.89 (ss, 1H), 7.30-7.13 (m, 4H), 6.19 (br. s, 2H), 5.06-4.87 (m, 3H), 4.38-4.25 (m, 1H), 4.13-4.06 (m, 1H), 4.01-3.76 (m, 3H), 3.70-3.35 (m, 2H), 2.31, 2.29 (ss, 3H), 1.32-1.30 (m, 3H), 1.24-1.21 (m, 3H), 1.18-1.15 (m, 6H). 31P: 25.08, 24.25 (ss, 1.14/1.00). [M+1]$^+$ 505.

Example 13

Anticancer Assay (WO 2006/100439)

Compounds synthesized as anti-cancer agents can each be each tested in leukaemic cell lines to assess their anticancer efficacy. The compounds can be tested using the MTS assay reagents from Promega (CellTiter96 Aqueous One solution proliferation assay). The compounds can be tested 5 μM (WO 2006/100439). Symbol, (+) indicates that the compound tested inhibits cellar growth greater than 50%.

Example 14

HCV Replicon Assay

The anti-HCV activity and toxicity of the exemplary compounds can be tested in two biological assays—a cell-based HCV replicon assay and cytotoxicity assay (WO 2007/027248).

I. Anti-HCV Assay

A human hepatoma cell line (Huh-7) containing replicating HCV subgenomic replicon with a luciferase reporter gene (luc-ubi-neo) was used to evaluate anti-HCV activity of the compounds. In this assay, level of luciferase signal correlates with the viral RNA replication directly. The HCV replicon-reporter cell line (NK/luc-ubi-neo) was cultured in DMEM medium supplemented with 10% fetal bovine serum and 0.5 mg/ml Geneticin (G418). Cells were maintained in a subconfluent state to ensure high levels of HCV replicon RNA synthesis.

To evaluate the antiviral activity of compounds, serial dilutions were prepared with concentrations ranging from 0.14 to 300 μM. Diluted compounds were transferred to a 96-well plate followed by the addition of replicon cells (6000 cells per well). Cells were incubated with the compounds for 48 h after which luciferase activity was measured. Reduction of luciferase signal reflected the decrease of HCV replicon RNA in the treated cells and used to determine the EC$_{50}$ value (concentration which yielded a 50% reduction in luciferase activity).

II. Cytotoxicity Assay

A Huh-7 cell line carrying a luciferase reporter gene (driven by a HIV LTR promoter) stably integrated into the chromosome was used to analyze the cytotoxic effect of the selected compounds. This cell line (LTR-luc) was maintained in DMEM medium with 10% FBS. Design of the cytotoxicity assay was similar to that of the HCV replicon assay. Reduction of luciferase activity in the treated cells correlated with the cytotoxic effect of the test compound and was used to calculate the $CC_{50}$ value (concentration that inhibited cell growth by 50%).

Example 15

Anti-HBV Assay

Compounds of the present invention can be assayed for anti-HBV activity according to any assay known to those of skill in the art.

Example 16

Compounds can be assayed for accumulation in liver cells of a subject according to any assay known to those of skill in the art. In certain embodiments, a liver cell of the subject can be used to assay for the liver accumulation of compound or a derivative thereof, e.g. a nucleoside, nucleoside phosphate or nucleoside triphosphate derivative thereof.

Example 17

Pharmacokinetic (PK) study of ester prodrug (FDURPAE), parent drug (FDUR) and prodrug in sodium salt form (FDURPAN) in rats were completed according to following procedure.

SD rats (250-300 g, male, N=24) were used for FDURPAE, FDUR and FDURPAN, purchased from SLAC Laboratory Animal Co. LTD Qualification No.: SCXK SH 2007-0005, 13264. FDURPAE (0.096 mmol, 52.17 mg/kg) and FDUR (0.096 mmol, 23.7 mg/kg) were dosed orally by gavage with a single dose of each compound to rats in a volume of 5 mL/kg in 0.5% carboxymethylcellulose sodium. FDURPAN (0.096 mmol, 50.24 mg) was dosed both orally or iv by gavage with a single dose to rats in a volume of 5 mL/kg in water. The animal was restrained manually at designated time points. Approximately 500 μL of blood/time point was collected into $K_2EDTA$ tube via cardiac puncture for terminal bleeding under anesthesia with Isoflurane. Blood samples were put on ice after collection and then centrifuged to obtain plasma sample (2000 g, 5 min, 4° C.) within 15 minutes of sampling. The blood samples were then centrifuged to obtain plasma sample (2000 g, 5 min, 4° C.). All the plasma samples were immediately quenched for protein precipitation. Liver samples were removed at designated time points by first sacrificing the animal by $CO_2$ inhalation, then perfusing the liver with ice cold saline and removing the left middle liver lobe, which was then snap frozen in dry ice. Liver samples were stored at approximately –80° C. until analysis. The liver homogenate was then processed for further analysis by LC/MS-MS. Plasma and liver samples were stored at approximately –80° C. until analysis.

Concentrations of parent drug and possible metabolites in both plasma and liver including FDURPAN (stable metabolite of FDURPAE), FDUR, 5FU and FDUR-MP were determined by LC/MS-MS, respectively. The results were summarized in Table 3.

TABLE 3

Rat plasma and liver PK profile after oral administration of FDURPAE (F5) and FDUR

| Tested Compds | Monitored Compds | plasma | | | Liver | | |
|---|---|---|---|---|---|---|---|
| | | Cmax (ng/mL) | Tmax (h) | AUC(inf) (ng · h/mL) | Cmax (ng/mL) | Tmax (h) | AUC(inf) (ng · h/mL) |
| FDURPAE (F5) | FDURPAN | 234 | 0.25 | 316 | 3673 | 0.25 | 5509 |
| (po) | FDUR | 17 | 0.25 | 26 | 747 | 0.25 | 1541 |
| (0.096 mmol) | 5FU | NA | NA | NA | 139 | 0.25 | 257 |
| | FDUR-MP | NA | NA | NA | 340 | 0.25 | 543 |
| FDUR | FDUR | 180 | 0.25 | 308 | NA | NA | NA |
| (po) | 5FU | 169 | 0.25 | 209 | 60 | 1.0 | 232 |
| (0.096 mmol) | FDUR-MP | 3.09 | 1.0 | 2.59 | 9.0 | 2.0 | NA |
| FDURPAN (F7) | FDURPAN | 32.9 | 0.5 | 203 | 122 | 0.25 | 213 |
| (po) | FDUR | 17.4 | 0.25 | 23.4 | NA | NA | NA |
| (0.096 mmol) | 5FU | 49.0 | 0.5 | 36.2 | 76.8 | 0.25 | 269 |
| | FDUR-MP | NA | NA | NA | NA | NA | NA |
| FDURPAN (F7) | FDURPAN | 5260 | 0.25 | 4216 | 7145 | 0.25 | 3128 |
| (iv) | FDUR | 663 | 0.25 | 243 | 2129 | 0.25 | 711 |
| (0.096 mmol) | 5FU | 40.9 | 0.25 | 26.3 | 567 | 0.25 | 2121 |
| | FDUR-MP | 150 | 0.25 | 42.7 | 1489 | 0.25 | 467 |
| F4 | FDUR | 39.7 | 1.0 | 41.4 | 49.8 | 8.0 | 838 |
| | 5FU | 14.2 | 1.0 | NA | 59.6 | 1.0 | NA |
| | FDUR-MP | NA | NA | NA | 54.7 | 1.0 | NA |

*NA: Not analyzed due to concentration below quantitation level.

Ester of prodrug F5 (FDURPAE) was rapidly hydrolyzed to more stable secondary prodrug F7 (FDURPAN) mediated by esterases so that FDURPAN instead of FDURPAE was monitored. Ester prodrug F5 (FDURPAE) can efficiently deliver drug substances including stable metabolite F7 (FDURPAN), parent drug (FDUR), metabolites (5FU and FDUR-MP) into the liver after oral administration. Only minimum secondary prodrug (FDURPAN), and parent drug (FDUR) could be detected in plasma. Ratio of $C_{max}$ for FDURPAN and FDUR in liver/plasma were 17 and 59, respectively. While metabolites 5FU and active drug FDUR-MP could not be detected in plasma at all. FDURPAE demonstrated excellent liver-targeting nature. Concentration of active drug (FDUR-MP) in the liver is comparable to that from iv administration of prodrug (FDURPAN) in sodium salt form.

PK Data for parent drug (FDUR) in Table 3 indicated that very limited drug-related compounds including parent drug (FDUR), metabolites (5FU and FDUR-MP) were detected in the liver after orally administration of FDUR. More drug substances including FDUR, 5FU and FDUR-MP were detected in plasma than in the liver. Overall, FDUR could not deliver drug substances into the liver target efficiently.

Prodrug (FDURPAN) in sodium salt form was dosed to rats both by oral or iv. Data in Table 3 indicated that FDURPAN could not deliver drug substances including FDURPAN, FDUR, 5FU and FDUR-MP to the liver target efficiently after oral administration probably due to its high clearance of water soluble drug. However, FDURPAN did deliver high levels of drug substances, in particular active monophosphate-FDUR-MP in the liver target after iv administration.

No 5FU or FDUR-MP was detected in both the liver and plasma after oral administration of equal molar of compound F4 probably due to its poor absorption.

Overall PK data in Table 3 suggest that ester prodrug of the present invention can be useful for the development of drugs for oral administration while prodrug in salt form can be better applied for development of drugs for iv administration for the treatment of liver associated diseases, such as hepatitis infection or liver cancer.

Figure 4:
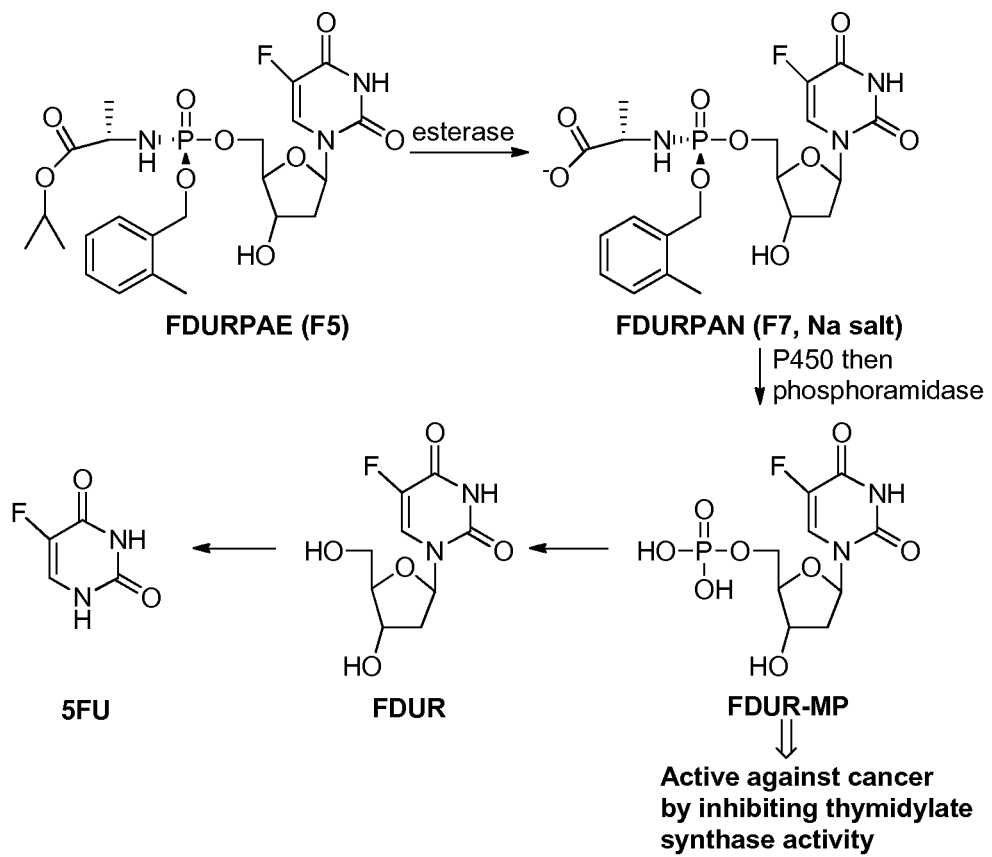
FIG. 4 illustrates proposed mechanism of action of prodrug F5 (FDURPAE).

Without intending to be bound by theory, FIG. 4 illustrates possible metabolic pathway for benzylic phosphoramidate or phosphonoamidate of the present invention. Ester prodrug F5 (FDURPAE) is hydrolyzed to a secondary prodrug F7 (FDURPAN) mediated by esterases. The FDURPAN is hydroxylated in the presence of P450 followed by releasing benzaldehyde and diacid which is further converted to the desired active nucleoside monophosphate mediated by phosphoramidase. The floxuridine (FDUR) monophosphate demonstrates anticancer activity by inhibiting activity of thymidylate synthase.

Prodrug technology disclosed herein can be applied in drug development to improve properties of parent drugs. Prodrug technology disclosed in the present invention is particularly useful for the development of drugs for the treatment of liver diseases, such as liver cancers, liver infections including hepatitis infections.

The following conclusions, inter alia, can be drawn about the present invention:

1. The present monophosphate prodrugs of nucleosides for the first time demonstrated the ability to deliver nucleoside phosphate into the liver selectively after oral administration.
2. The technology of the present monophosphate prodrugs of nucleosides can be used to convert drugs that previously can only be administered via injection to orally available drugs.
3. The present monophosphate prodrugs of nucleosides were for the first time prepared as single isomers through asymmetric synthesis, which may find general practical utility for the drug design and development.
4. The present monophosphate prodrugs of nucleosides were designed and discovered to be activated by esterase and P450 enzymes in the liver, which can be considered as double-liver-targeting prodrugs and will be particularly useful for the development of orally available drugs for treating liver diseases including hepatitis infections and liver cancers.
5. Monocarboxylic acids and salts of nucleoside phosphoramidate prodrugs were prepared for the first time as stable water soluble drug substances.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. All such variations are intended to be included within the scope of the following claims. All references cited herein, either patent or non-patent literature, are incorporated by reference in their entirety.

What is claimed is:

1. A compound of formula:

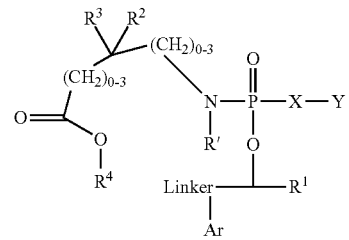

or a pharmaceutically acceptable salt or solvate thereof, wherein:

X is oxygen (O) or —$CH_2$—;

Y is a nucleoside, acyclonucleoside, or C-nucleoside moiety;

R', $R^1$, $R^2$, and $R^3$ are each independently selected from the group consisting of hydrogen and substituted or unsubstituted alkyl, aryl, alkynyl, alkenyl, cycloalkyl, heterocyclyl, and heteroaryl groups, wherein said heterocyclyl and heteroaryl group each comprises one to three heteroatoms independently selected from O, S, and N, or alternatively, $R^2$ and $R^3$, together with the carbon atom to which they are attached, form an optionally substituted 3- to 8-membered ring;

$R^4$ is selected from the group consisting of hydrogen, and substituted or unsubstituted alkyl, aryl, alkynyl, alkenyl, cycloalkyl, heterocyclyl, and heteroaryl groups, metal ions, and ammonium ions;

Ar is substituted $C_6$-$C_{10}$ aryl or optionally substituted 5- to 10-membered heteroaryl comprising one to three heteroatoms independently selected from O, S, and N; and the "linker" is selected from a bond and optionally substituted $C_1$-$C_3$ alkylene, vinyl, ethynyl, arylene, and heteroarylene, wherein the heteroarylene comprises one to three heteroatoms independently selected from O, S, and N.

2. The compound of claim 1, having formula:

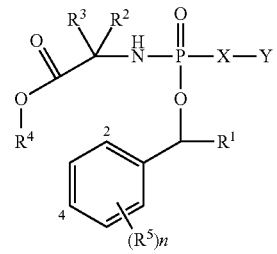

or a pharmaceutically acceptable prodrug, salt, or solvate thereof, wherein:

$R^1$, $R^2$, $R^3$, $R^4$, X and Y are defined as in claim 1;

n is 1, 2, 3, 4, or 5;

$R^5$ at each occurrence is independently selected from halogen (F, Cl, Br, I) and optionally substituted acyloxy, acyl- NH—, methoxy, alkyl, alkyloxy, alkylamino, cycloalkyl, cycloalkyloxy, cycloalkylamino, aryl, aryloxy, arylamino, and arylalkyl.

3. The compound of claim 2, having the formula:

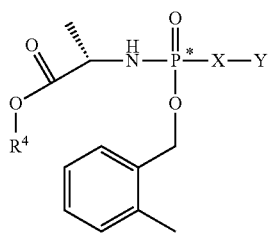

or a pharmaceutically acceptable prodrug, salt, or solvate thereof, wherein:

$R^4$, X and Y are defined as in claim 2.

4. The compound of claim 3, wherein X is —O— or —CH$_2$—, having the formula:

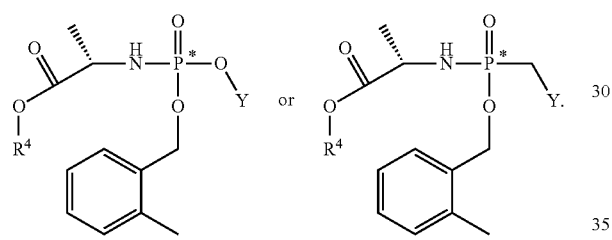

or a pharmaceutically acceptable prodrug, salt, or solvate thereof, wherein:

$R^4$ and Y are defined as in claim 3.

5. The compound of claim 3, wherein X is —O— or —CH$_2$—, having the formula:

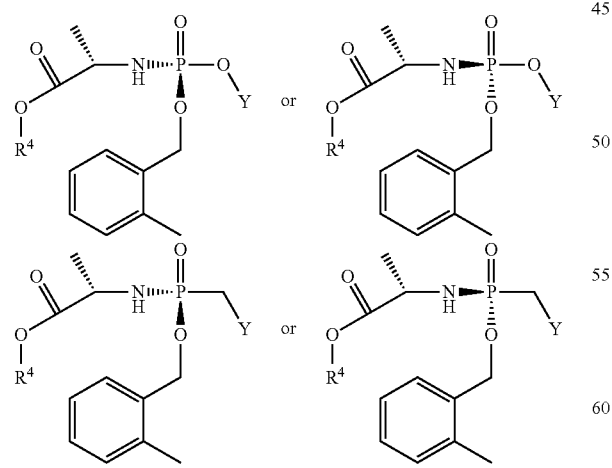

or a pharmaceutically acceptable prodrug, salt, or solvate thereof, wherein:

$R^4$ and Y are defined as in claim 3.

6. The compound of claim 1, wherein Y is a nucleoside moiety, or a pharmaceutically acceptable salt or solvate thereof.

7. The compound of claim 1, wherein $R^4$ is $M^+$, and Y is a nucleoside moiety, or a pharmaceutically acceptable salt or solvate thereof, wherein $M^+$ is selected from the group consisting of $NH_4^+$, $K^+$, $Na^+$, $Ca^{2+}$, and $Mg^{2+}$.

8. The compound of claim 1, wherein X is O, and Y is a nucleoside moiety of formula:

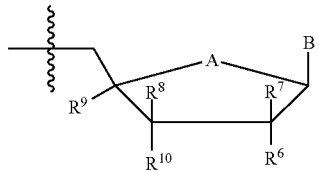

or a pharmaceutically acceptable salt or solvate thereof, wherein:

"A" is selected from the group consisting of O, S, CH$_2$, C=CH$_2$, and CF$_2$;

$R^6$ and $R^7$ are independently selected from H, OH, CH$_3$O, F, Cl, Br, I, CN, N$_3$, methyl, ethyl, vinyl, ethynyl, chlorovinyl, fluoromethyl, difluoromethyl, and trifluoromethyl, or alternatively, $R^6$ and together form a vinylidene group

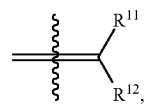

wherein $R^{11}$ and $R^{12}$ are each independently hydrogen, halogen, methyl, or N$_3$;

$R^8$ is selected from the group consisting of H, methyl, ethyl, vinyl, ethynyl, chlorovinyl, fluoromethyl, difluoromethyl, and trifluoromethyl;

$R^9$ is selected from the group consisting of H, CN, N$_3$, methyl, ethyl, vinyl, ethynyl, chlorovinyl, fluoromethyl, difluoromethyl, and trifluoromethyl;

$R^{10}$ is selected from the group consisting of H, OH, F, cyano, and azido;

or alternatively, one of $R^8$ or $R^{10}$ together with one of $R^6$ or $R^7$ forms a bond;

"B" is a pyrimidine or purine moiety selected from formulae B-1 and B-2:

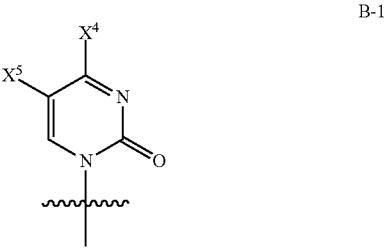

-continued

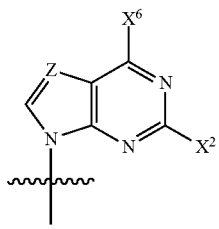

B-2 wherein $X^2$ is selected from the group consisting of H, $NH_2$, NHMe, $NMe_2$, and halogen (I, Br, Cl, F);

$X^4$ is $NH_2$ or OH;

$X^5$ is selected from the group consisting of halogen (I, Br, Cl, F), OH, $NH_2$, methyl, vinyl, alkyl, 2-bromovinyl, and ethynyl;

$X^6$ is selected from the group consisting of H, OH, alkyloxy, aryloxy, alkyloxy, alkylthio,arylthio, cyclic alkylthio, thienyl, furyl, alkylamino, dialkylamino, arylamino, aryl alkylamino, cyclic alkylamino, and cyclopropylamino;

Z is nitrogen (N) or $CX^7$; and $X^7$ is selected from the group consisting of H, vinyl, ethynyl, and halogen;

wherein any amino ($NH_2$) and hydroxyl (OH) groups are optionally protected.

9. The compound of claim 8, wherein Y is a nucleoside moiety:

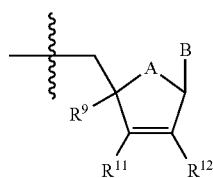

or a pharmaceutically acceptable salt or solvate thereof, wherein:

B, A, and $R^9$ are defined as in claim 8; and $R^{11}$ and $R^{12}$ are independently selected from H, $N_3$, F, CN, $CH_3$, alkyl, and vinyl.

10. The compound of claims 1, wherein X is O, Y is a nucleoside moiety selected from formulae:

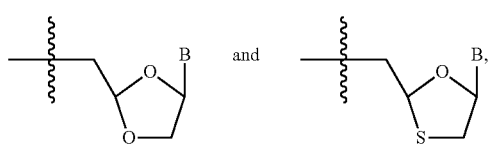

or a pharmaceutically acceptable salt or solvate thereof, wherein:

"B" is a pyrimidine or purine moiety selected from formulae B-1 and B-2:

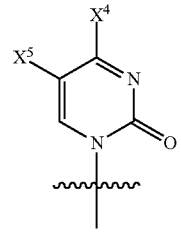

B-1

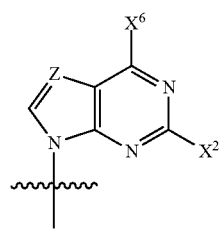

B-2 wherein $X^2$ is selected from the group consisting of H, $NH_2$, NHMe, $NMe_2$, and halogen (I, Br, Cl, F);

$X^4$ is $NH_2$ or OH;

$X^5$ is selected from the group consisting of halogen (I, Br, Cl, F), OH, $NH_2$, methyl, vinyl, alkyl, 2-bromovinyl, and ethynyl;

$X^6$ is selected from the group consisting of H, OH, alkyloxy, aryloxy, alkyloxy, alkylthio,arylthio, cyclic alkylthio, thienyl, furyl, alkylamino, dialkylamino, arylamino, aryl alkylamino, cyclic alkylamino, and cyclopropylamino;

Z is nitrogen (N) or $CX^7$; and $X^7$ is selected from the group consisting of H, vinyl, ethynyl, and halogen;

wherein any amino ($NH_2$) and hydroxyl (OH) groups are optionally protected.

11. The compound of claim 1, or a pharmaceutically acceptable salt or solvate thereof, wherein X is $CH_2$, or a pharmaceutically acceptable salt or solvate thereof.

12. The compound of claim 1, or a pharmaceutically acceptable salt or solvate thereof, wherein X is O, and Y is a moiety of an acyclic nucleoside selected from the group consisting of acyclovir, ganciclovir and pencyclovir.

13. The compound of claim 1, or a pharmaceutically acceptable salt or solvate thereof, wherein X is O, and Y is a moiety of a C-nucleoside comprising a nucleic base and a sugar moiety connected with each other through a carbon-carbon bond.

14. The compound of claim 8, or a pharmaceutically acceptable salt or solvate thereof, wherein the —X—Y is a moiety of a compound selected from compounds of formulas:

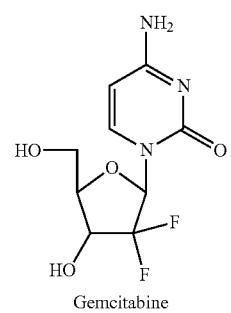

Gemcitabine

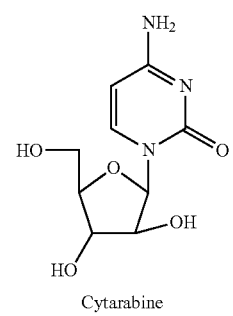

Cytarabine

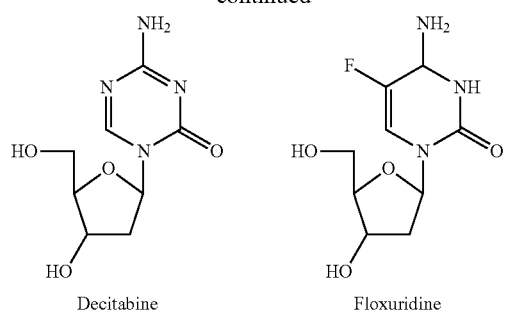
Decitabine          Floxuridine
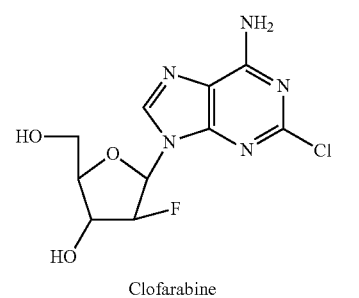
Clofarabine
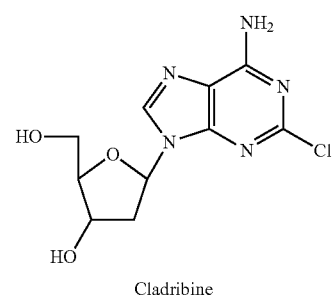
Cladribine
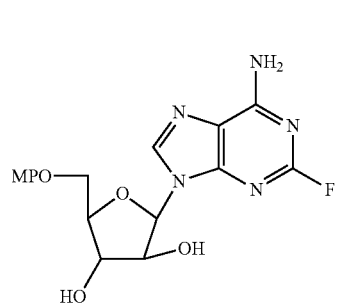
Fludarabine
MP: monophosphate
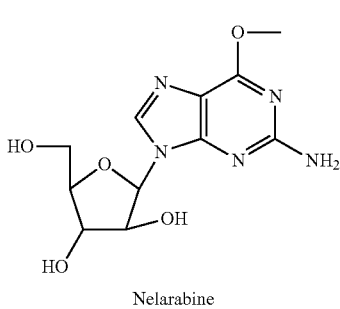
Nelarabine
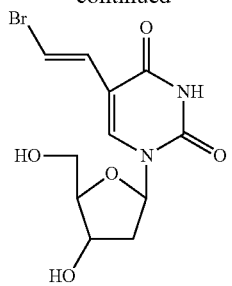
BVDU
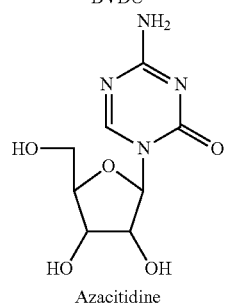
Azacitidine
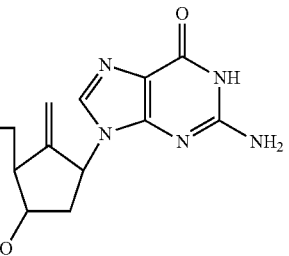
Entecavir
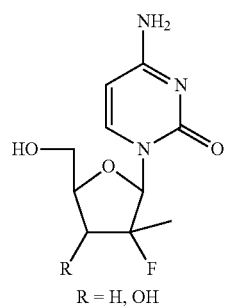
R = H, OH
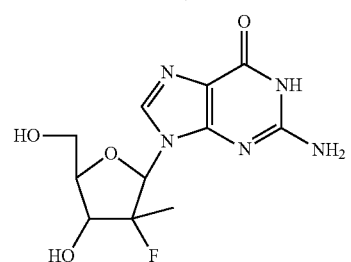
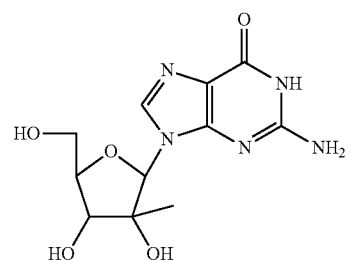

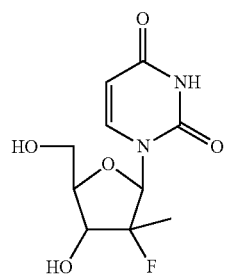
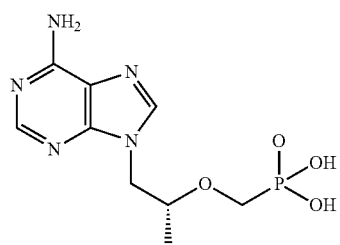
Tenofovir
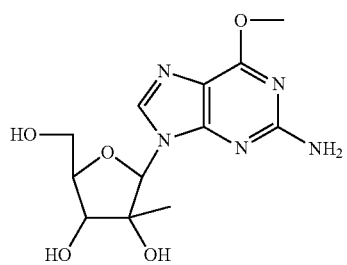
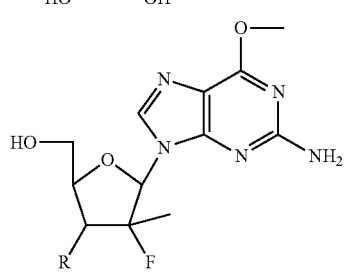
R = H, OH
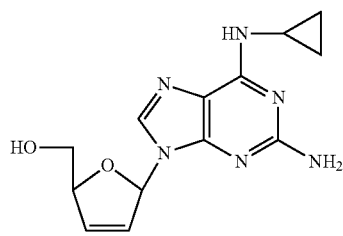
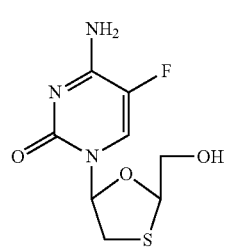
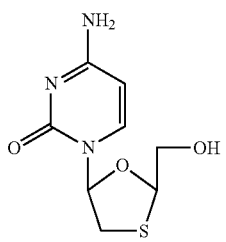
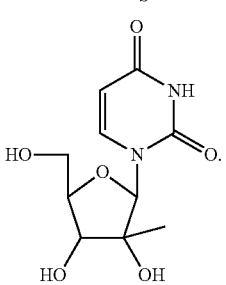
15. The compound of claim 1 selected from the group consisting of formulas:
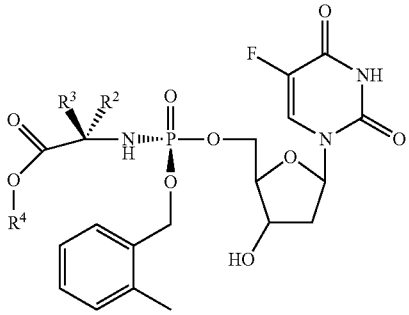
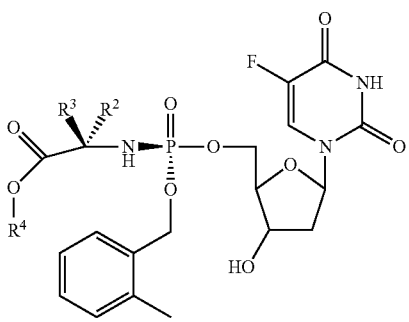
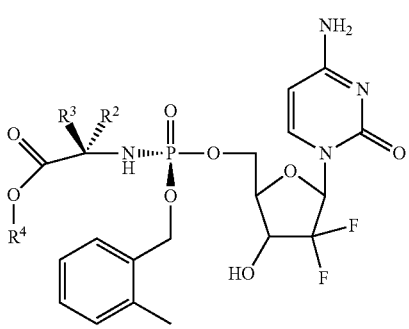

65
-continued
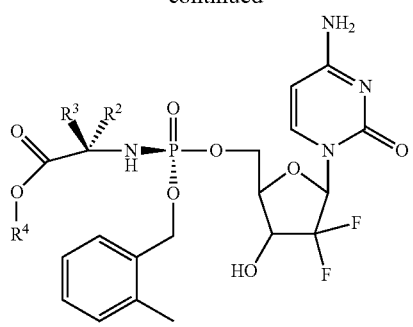
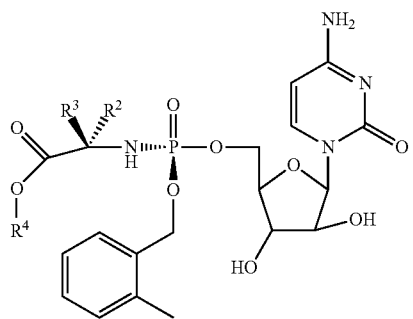
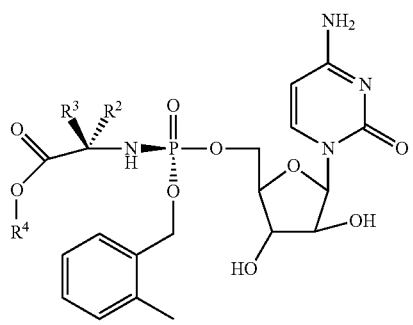
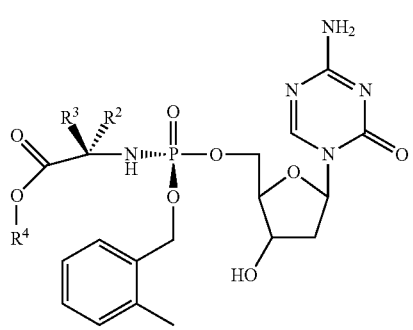
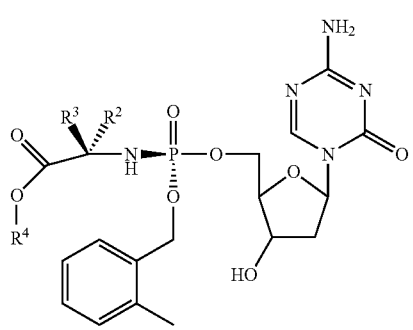
66
-continued
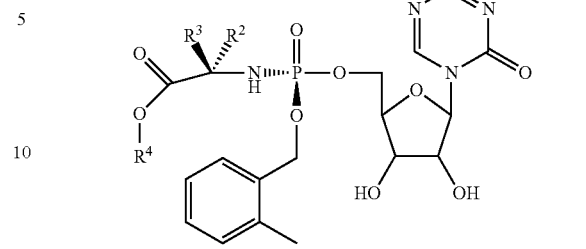
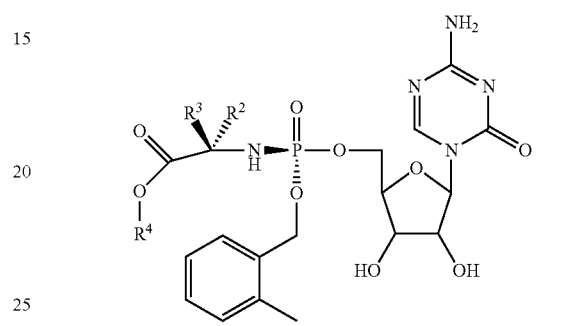
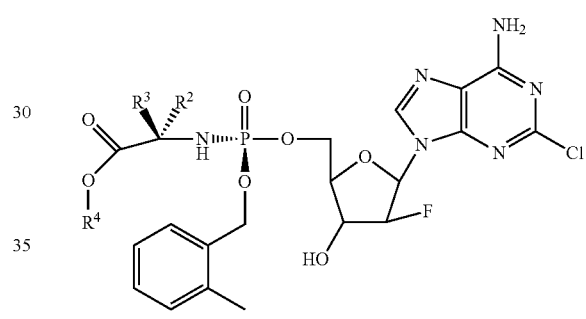
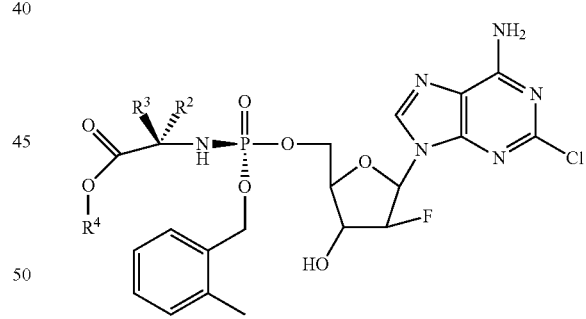
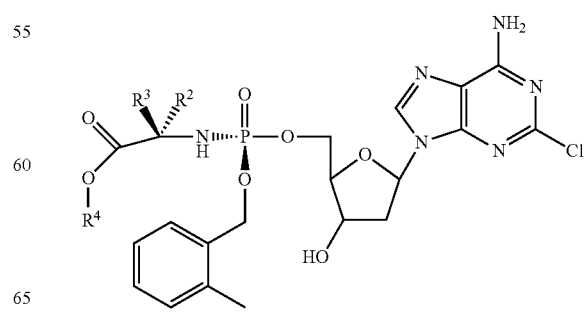

67
-continued
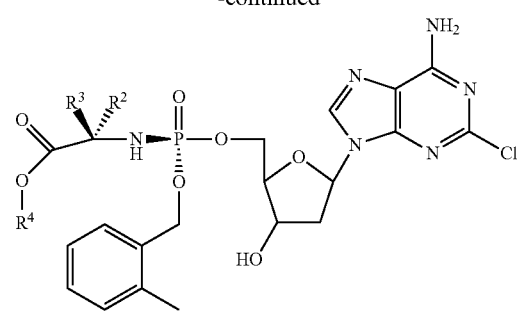
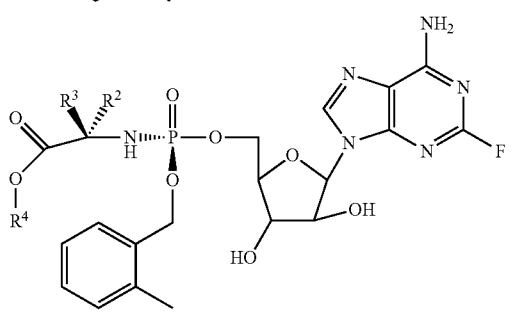
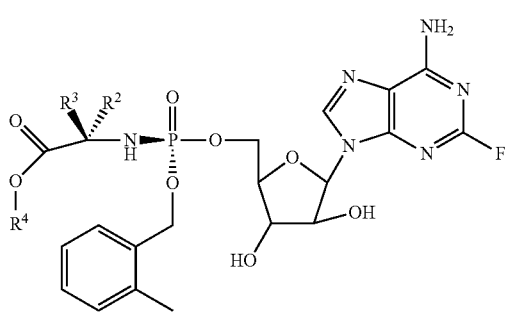
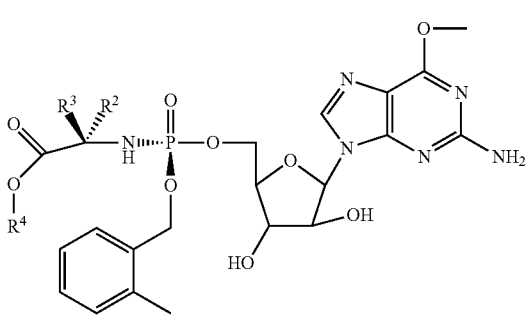
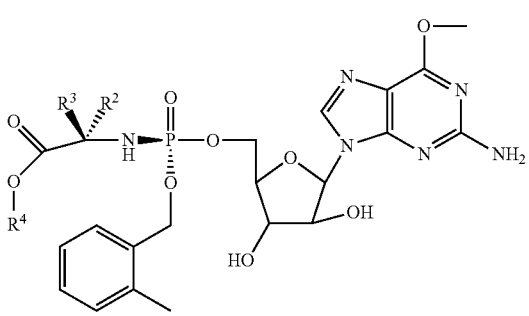
68
-continued
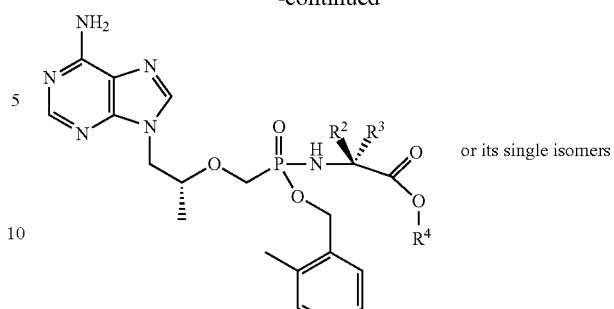
or its single isomers
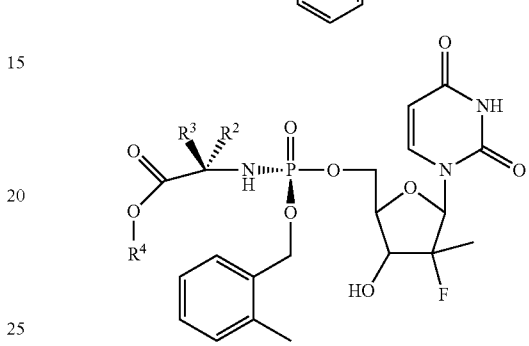
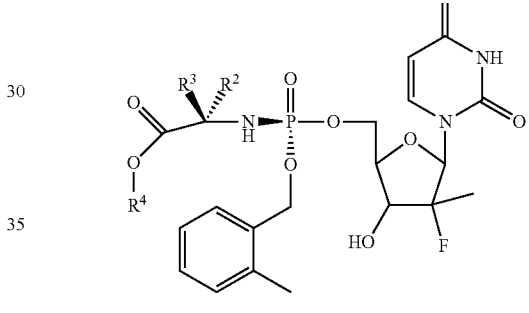
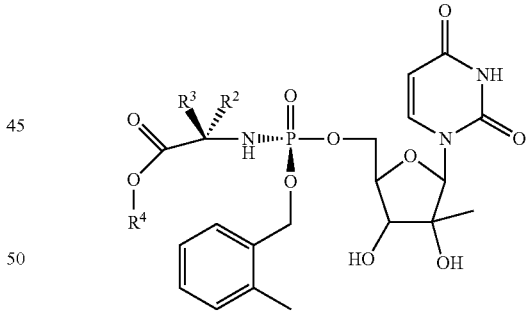
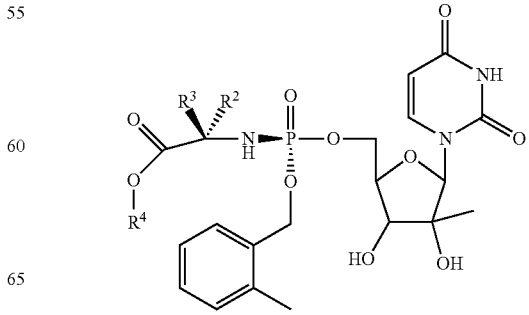

69
-continued
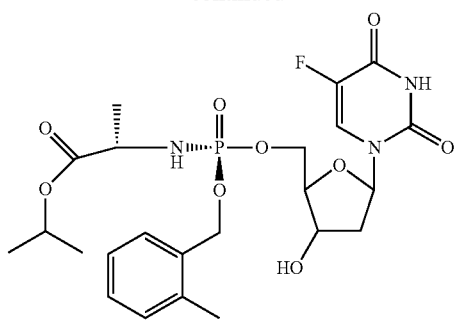
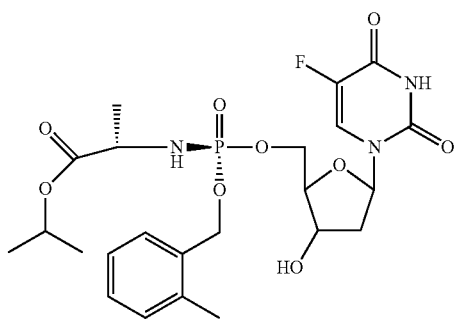
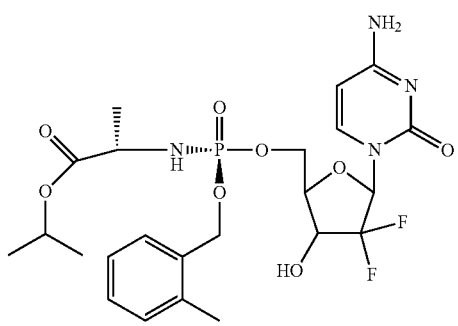
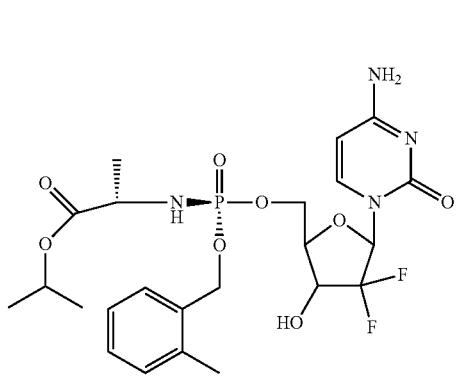 [SMILES: Cc1ccccc1CO[P@@](=O)(N[C@@H](C)C(=O)OC(C)C)OCC1OC(n2ccc(=O)[nH]c2=O)C(C)(O)C1O]
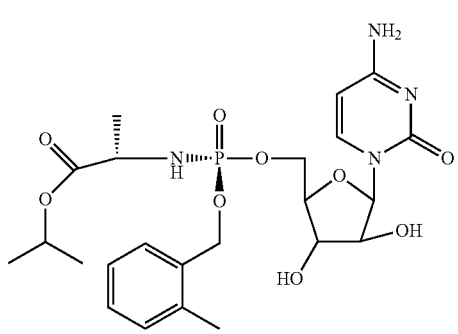
70
-continued
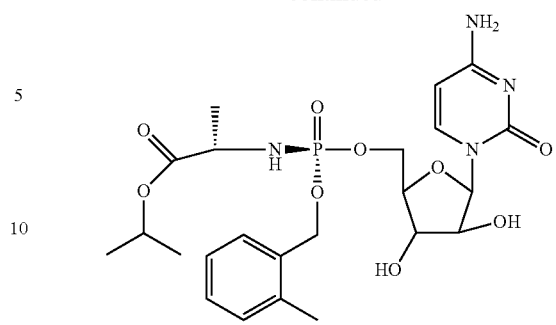
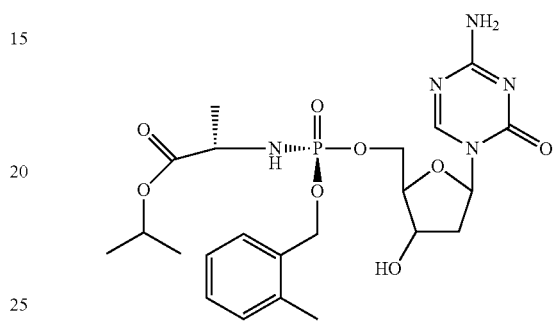
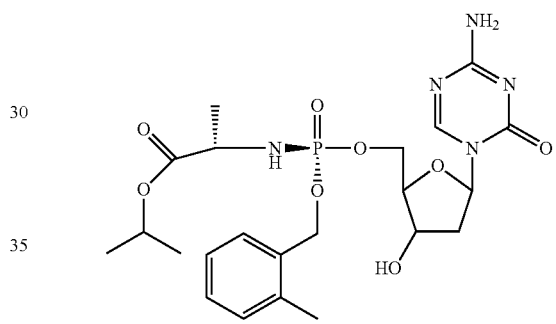
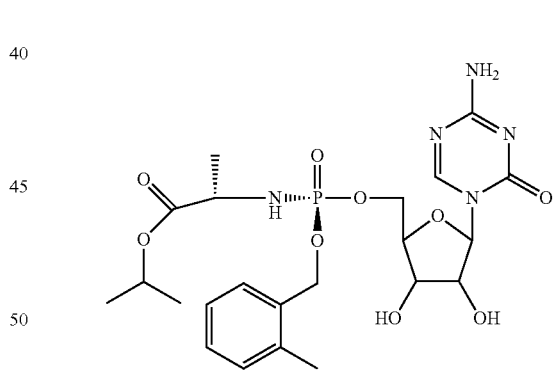
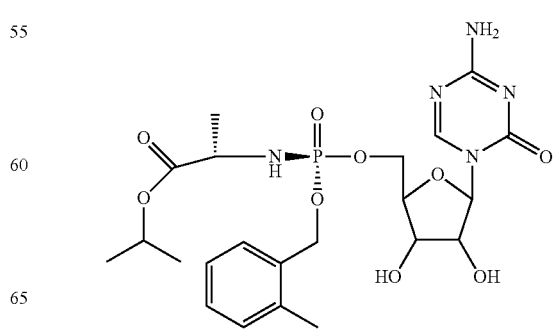

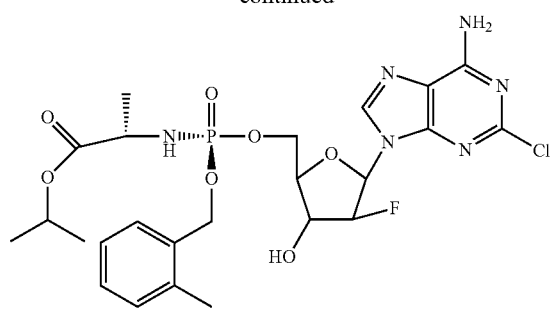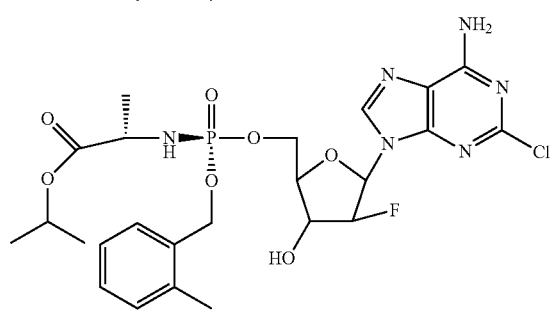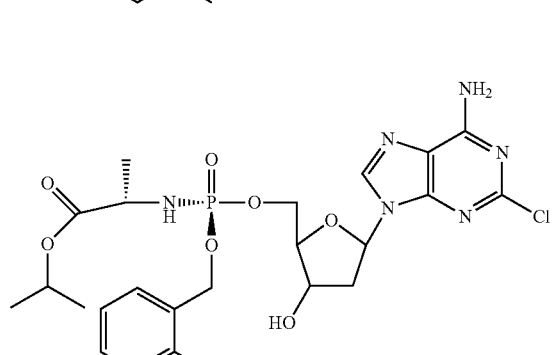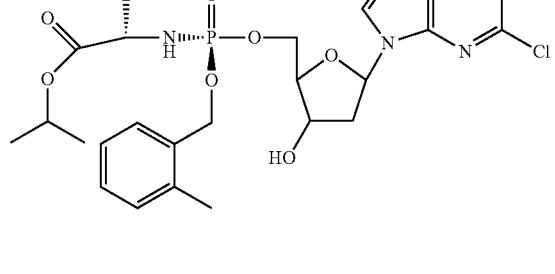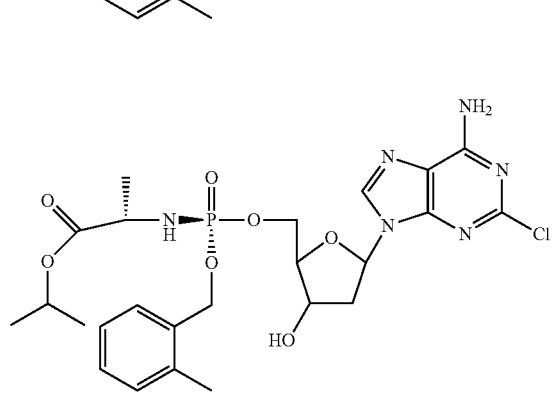
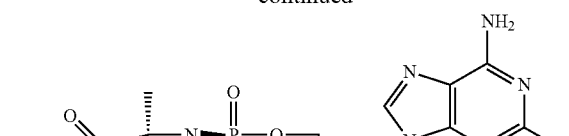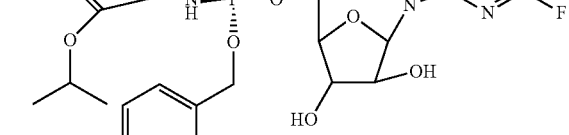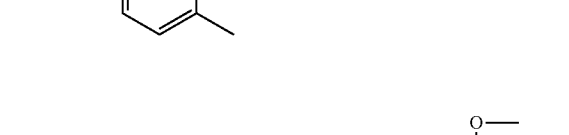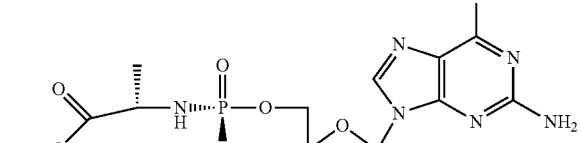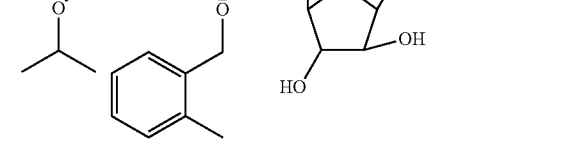 or its single isomers
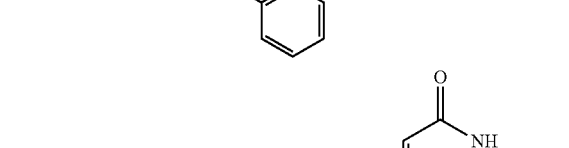

-continued

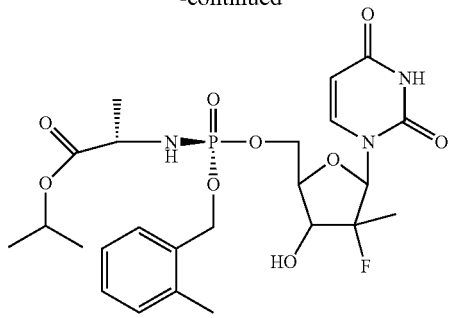

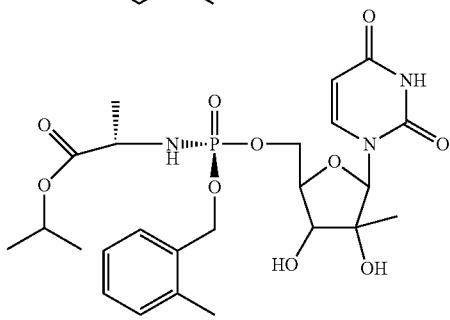

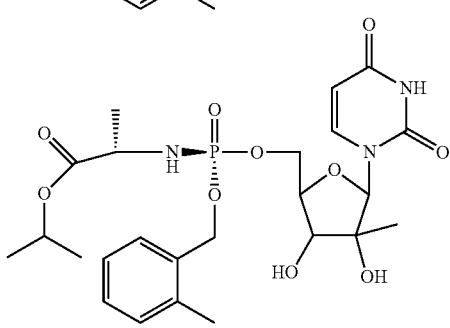

or a pharmaceutically acceptable salt or solvate thereof.

16. A pharmaceutical composition comprising a compound of claim 1, or a pharmaceutically acceptable salt or solvate thereof, and a pharmaceutically acceptable carrier or diluent.

17. A method of treating a viral infection or cancer, comprising administration of a compound of claim 1, or a pharmaceutically acceptable salt or solvate thereof, to a patient in need of the treatment.

18. A process for preparing a compound of claim 3, or a pharmaceutically acceptable salt or solvate thereof, comprising the steps of:

a) reacting a compound of formula:

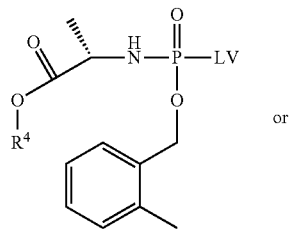

wherein the LV is a leaving group and $R^4$ is isopropyl or defined as in claim 3, with pentafluorophenol in the presence of a base to give a diastereomerically enriched compound of formula:

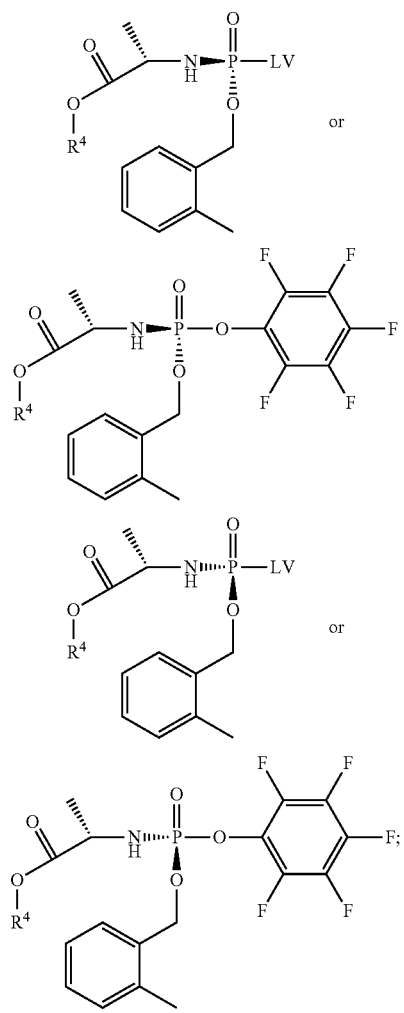

and b) reacting diastereomerically enriched compound obtained from step a) with a nucleoside in the presence of a base to give the compound of claim 3 in ester or salt form selected from formulas:

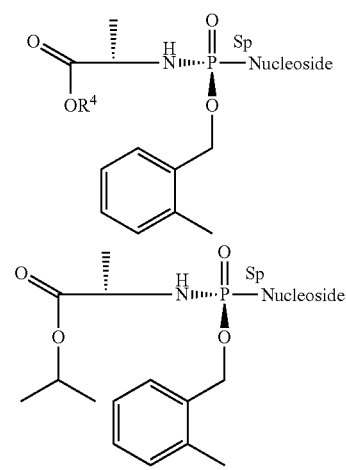

-continued

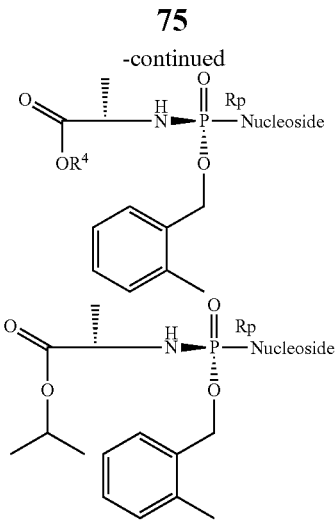

wherein R⁴ is isopropyl or defined as in claim 3.

19. A compound useful for preparing the compound of claim 1, selected from the group consisting of formulas:

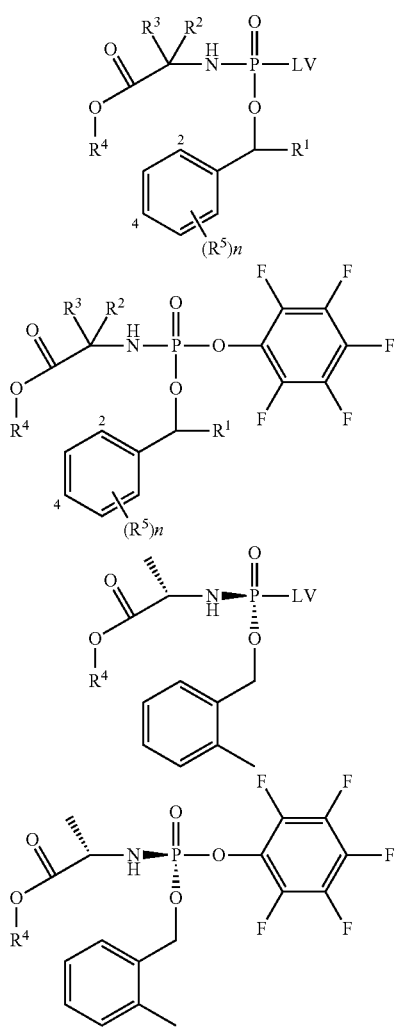

-continued

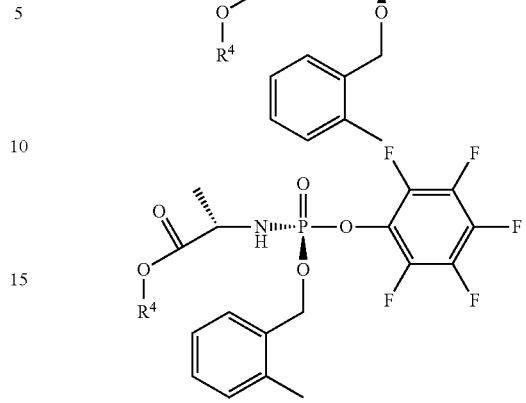

wherein LV is a leaving group, and $R^1$, $R^2$, $R^3$, $R^4$, $R^5$ and n are defined as in claim 1.

20. A method of enhancing bioavailability and/or liver-targeting property of an alcohol drug, comprising protecting at least one hydroxyl group of said alcohol-containing drug with a phosphoramidate moiety of formula:

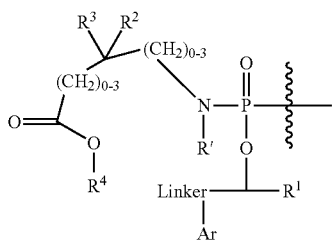

wherein:
R', $R^1$, $R^2$, and $R^3$ are each independently selected from the group consisting of hydrogen and substituted or unsubstituted alkyl, aryl, alkynyl, alkenyl, cycloalkyl, heterocyclyl, and heteroaryl groups, wherein the heterocyclyl and heteroaryl group each comprises one to three heteroatoms independently selected from O, S, and N, or, alternatively, $R^2$ and $R^3$ together with the carbon atom to which they are attached form an optionally substituted 3- to 8-membered ring;

$R^4$ is selected from the group consisting of hydrogen and substituted or unsubstituted alkyl, aryl, alkynyl, alkenyl, cycloalkyl, heterocyclyl, and heteroaryl groups, metal ions, and ammonium ions;

Ar is substituted $C_6$-$C_{10}$ aryl or optionally substituted 5- to 10-membered heteroaryl comprising one to three heteroatoms independently selected from O, S, and N; and the "linker" is selected from a bond and optionally substituted $C_1$-$C_3$ alkylene, vinyl, ethynyl, arylene and heteroarylene, wherein the heteroaryl comprises one to three heteroatoms independently selected from O, S, and N.

\* \* \* \* \*